(12) United States Patent
O'Day et al.

(10) Patent No.: US 9,606,106 B2
(45) Date of Patent: Mar. 28, 2017

(54) NMR-BASED METABOLITE SCREENING PLATFORM

(71) Applicants: THE CHILDREN'S MEDICAL CENTER CORPORATION, Boston, MA (US); PRESIDENT AND FELLOWS OF HARVARD COLLEGE, Cambridge, MA (US)

(72) Inventors: Elizabeth M. O'Day, Braintree, MA (US); Judy Lieberman, Brookline, MA (US); Gerhard Wagner, Chestnut Hill, MA (US)

(73) Assignees: Children's Medical Center Corporation, Boston, MA (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/377,257

(22) PCT Filed: Feb. 11, 2013

(86) PCT No.: PCT/US2013/025628
§ 371 (c)(1),
(2) Date: Aug. 7, 2014

(87) PCT Pub. No.: WO2013/120099
PCT Pub. Date: Aug. 15, 2013

(65) Prior Publication Data
US 2015/0005243 A1   Jan. 1, 2015

Related U.S. Application Data

(60) Provisional application No. 61/597,298, filed on Feb. 10, 2012.

(51) Int. Cl.
| | |
|---|---|
| *G01N 33/50* | (2006.01) |
| *G01N 24/08* | (2006.01) |
| *G01R 33/46* | (2006.01) |
| *G01R 33/465* | (2006.01) |
| *A61B 5/055* | (2006.01) |

(52) U.S. Cl.
CPC ......... *G01N 33/5011* (2013.01); *G01N 24/08* (2013.01); *G01N 33/5005* (2013.01); *G01N 33/5038* (2013.01); *G01R 33/465* (2013.01); *G01R 33/4633* (2013.01); *A61B 5/055* (2013.01); *G01N 2458/15* (2013.01); *G01N 2500/10* (2013.01); *G01N 2570/00* (2013.01)

(58) Field of Classification Search
CPC ................................................. G01N 33/5038
See application file for complete search history.

(56) References Cited

U.S. PATENT DOCUMENTS

| | | | |
|---|---|---|---|
| 4,703,267 | A | 10/1987 | Maudsley |
| 2007/0141712 | A1 | 6/2007 | Ludemann et al. |
| 2008/0081375 | A1 | 4/2008 | Tesiram et al. |
| 2010/0248279 | A1 | 9/2010 | Yamauchi et al. |

FOREIGN PATENT DOCUMENTS

| | | |
|---|---|---|
| JP | S62-72347 | 4/1987 |
| JP | H08-271602 | 10/1996 |
| JP | 2000-014657 | 1/2000 |
| JP | 2005-514959 | 5/2005 |
| JP | 2005-181332 | 7/2005 |
| JP | 2006-053099 | 2/2006 |
| JP | 2006-053100 | 2/2006 |
| JP | 2006-138666 | 6/2006 |
| JP | 2006-194761 | 7/2006 |
| JP | 2007-526245 | 9/2007 |
| JP | 2008-504525 | 2/2008 |
| JP | 2009-077710 | 4/2009 |
| WO | 02/094869 | 11/2002 |
| WO | WO03062458 | 7/2003 |
| WO | WO 2005/072780 | 8/2005 |
| WO | WO 2006/002243 | 1/2006 |
| WO | WO 2008/087822 | 7/2008 |

OTHER PUBLICATIONS

Eichinger et al. Phytochemistry, 1999, 51:223-236.*
Miccheli et al. Biochimie, 2006, 88:437-448.*
Massimi et al. Biochimica et Biophysica Acta., 2012, 1820:1-8.*
Barton et al., "High-throughput 1H NMR-based metabolic analysis of human serum and urin for large-scale epidemiological studies: validation study," International Journal of Epidemiology, 37(1):i31-i40 (2008).
Carrola et al., "Metabolic signatures of lung cancer in biofluids: NMR-based metabonomics of urine," Journal of Proteome Research, 10(1):221-230 (2011).
Hyberts et al., "Ultrahigh-Resolution $^{1}H$-$^{13}C$ HSQC Spectra of Metabolite Mixtures Using Nonlinear Sampling and Forward Maximum Entropy Reconstruction," J. Am. Chem. Soc., 129:5108-5116 (2007).
International Preliminary Report on Patentability issued in PCT/US2013/025628 on Aug. 12, 2014 (11 pages).
International Search Report and Written Opinion issued in PCT/US2013/025628 on May 14, 2013 (16 pages).

(Continued)

*Primary Examiner* — Bin Shen
(74) *Attorney, Agent, or Firm* — Fish & Richardson P.C.

(57) ABSTRACT

Methods that enable one to specifically measure the metabolic product of a particular molecule in relatively few cells, e.g. primary cells, are described. The methods involve optionally preloading cells with labeled substrate (e.g. labeled by $^{13}C$, $^{15}N$, or $^{31}P$). The methods allow for easy identification of metabolites that are differentially generated in cells of different phenotypes. The new methods for unbiased multi-dimensional NMR screening and rapid and efficient analysis of the NMR screening identify differentially expressed metabolites in different cell or tissue types. Analysis of the differentially expressed metabolites can present unique druggable targets to which small molecule therapeutics can be designed.

16 Claims, 25 Drawing Sheets

(56) References Cited

OTHER PUBLICATIONS

Jeannerat, D., "Computer optimized spectral aliasing in the indirect dimension of 1H-13C heteronuclear 2D NMR experiments. A new algorithm and examples of applications to small molecules," Journal of Magnetic Resonance, 186(1):112-122 (2007).

Maciejewski et al., "Random phase detection in multidimensional NMR," PNAS, 108(40):16640-16644 (2011).

Stern et al., "NMR data processing using iterative thresholding and minimum 11-norm reconstruction," Journal of Magnetic Resonance, 188(2):295-300 (2007).

Bagshawe et al., "Immunogenicity of L 1210 Murine Leukemia Cells after Treatment with Neuraminidase", Nature (1968) Retrieved from the Internet: URL:http://www.nature.com/nature/journal/v218,n5148/pdf/2181254a0.pdf [retrieved on Mar. 1, 2016], 6 pages.

Chikayma et al., "Systematic NMR Analysis of Stable Isotope Labeled Metabolite Mixtures in Plant and Animal Systems: Coarse Grained Views of Metabolic Pathways", PLOS ONE 3(11)25: e3805 (Nov. 2008).

European Search Report in European Application No. 13746933.4, dated Mar. 2, 2016, 8 pages.

Kim et al., "A sialic acid-binding lectin from the legume *Maackia fauriei*: comparison with lectins from M. amurensis", Plant Science, 167(6): 1315-1321 (Dec. 2004).

Wu et al., "Soyasaponin I, a potent and specific sialyltransferase inhibitor", Biochemical and Biophysical Research Communications, Academic Press Inc., Orlando, FL., U.S. 284:466-469 (Jun. 2001).

Japanese Office Action in Japanese Application No. 2014-556791, dated Dec. 6, 2016, 9 pages (with English translation).

\* cited by examiner

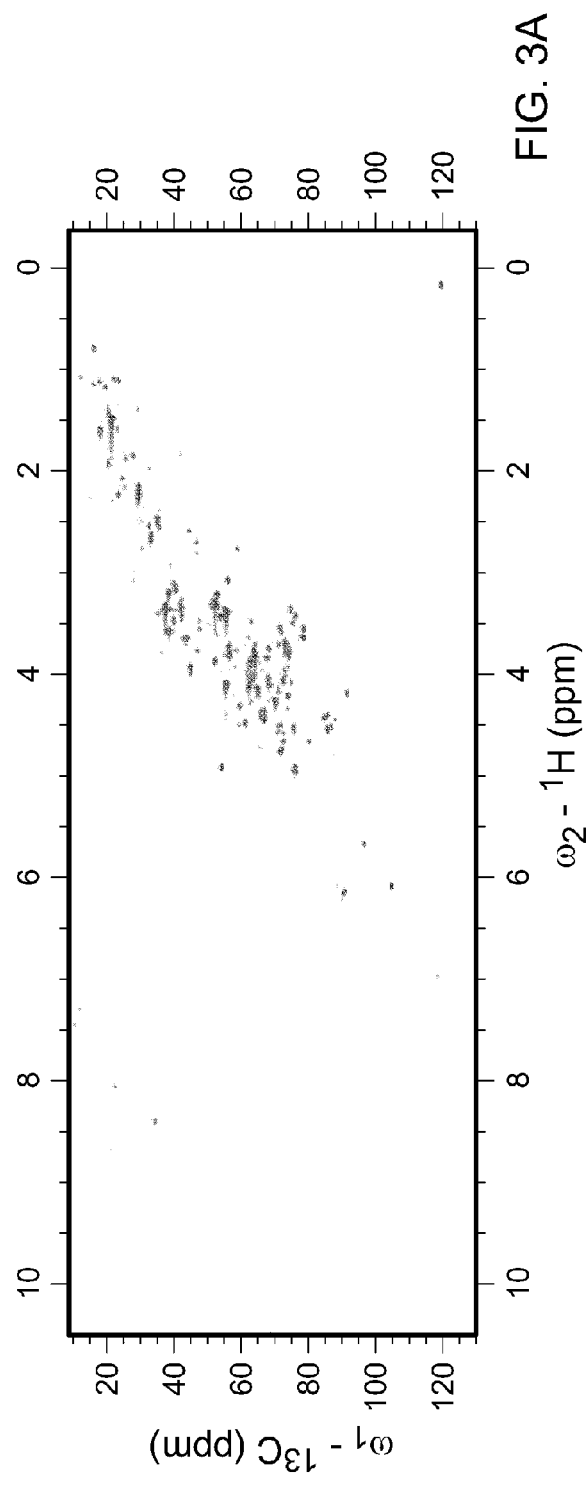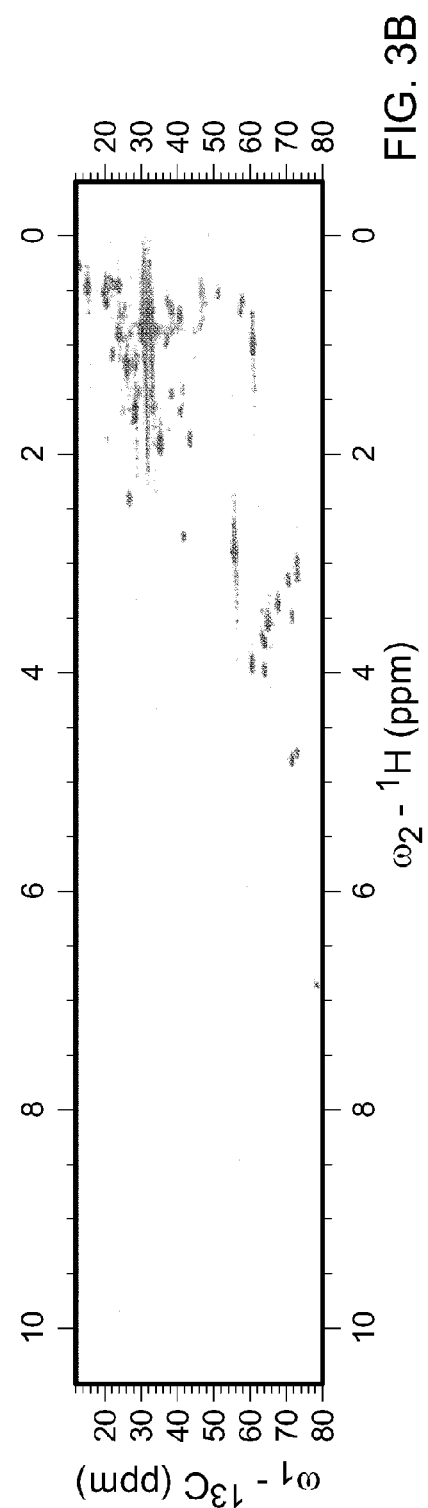
FIG. 3A
FIG. 3B

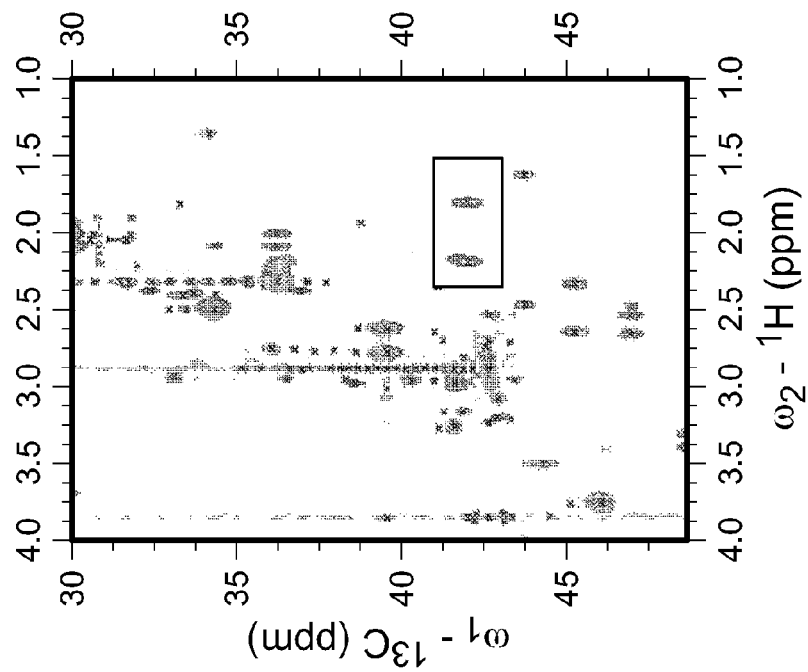
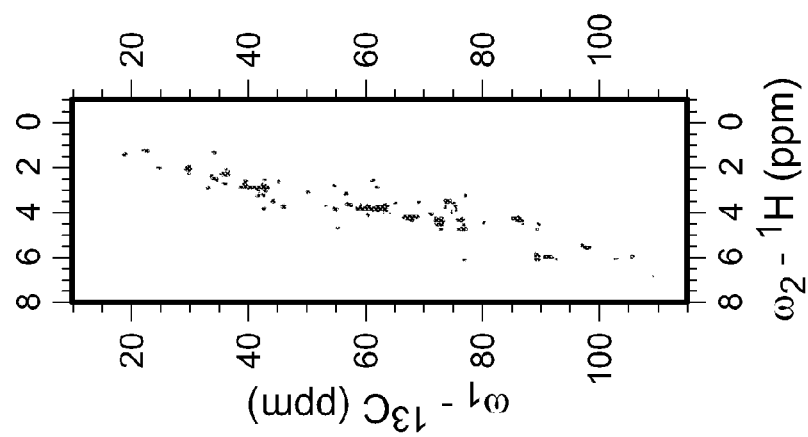
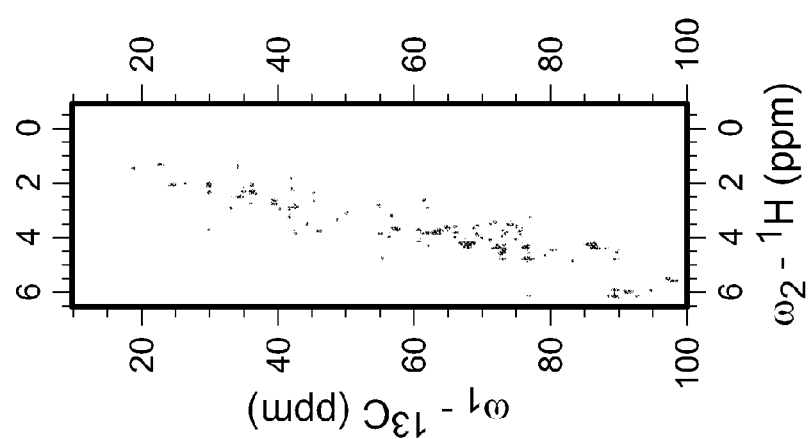
FIG. 7D
FIG. 7B
FIG. 7A

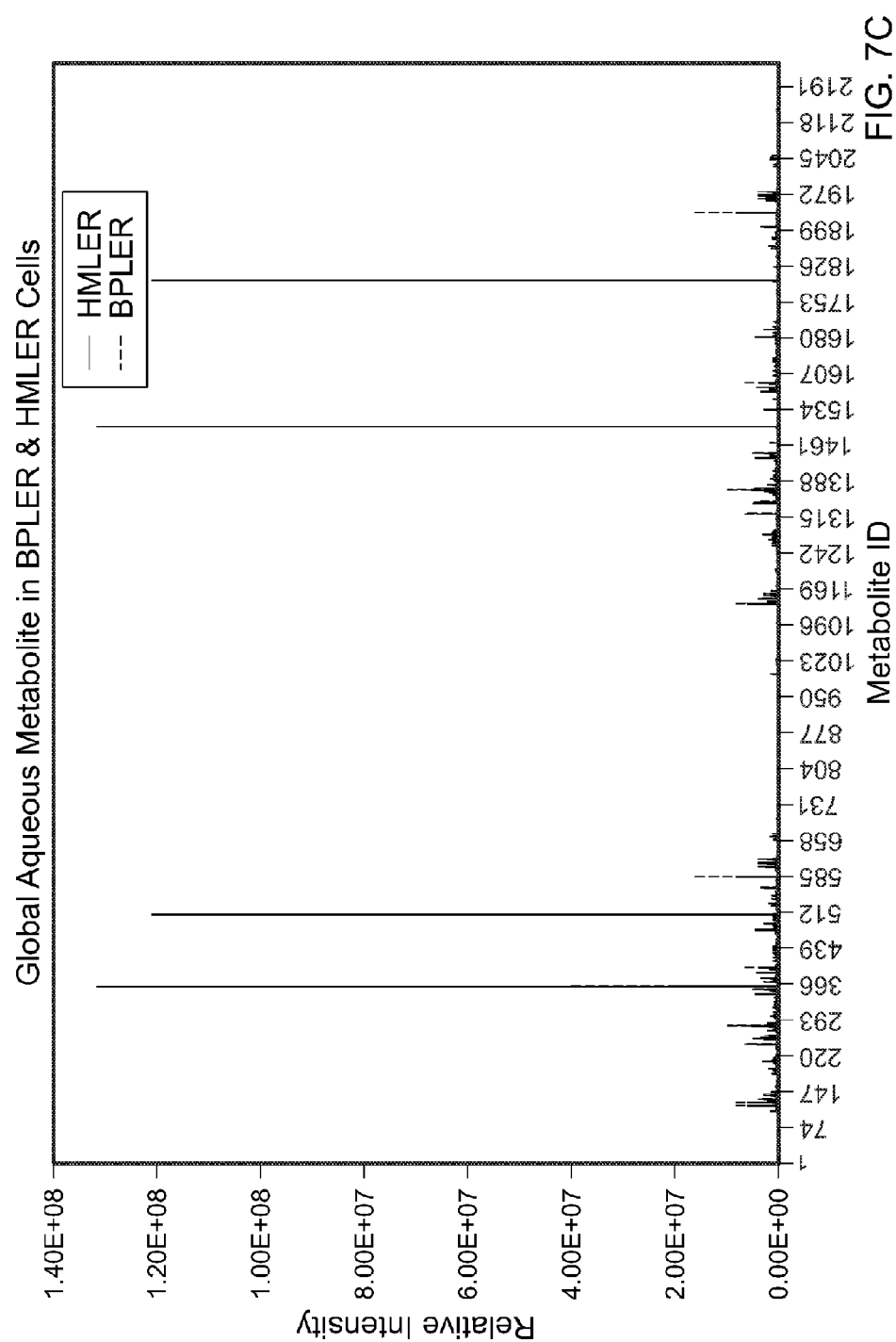

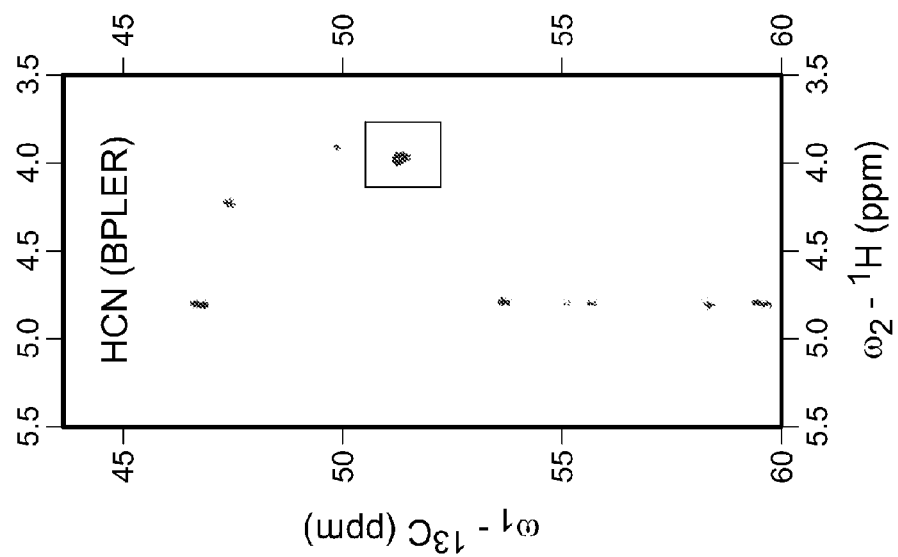
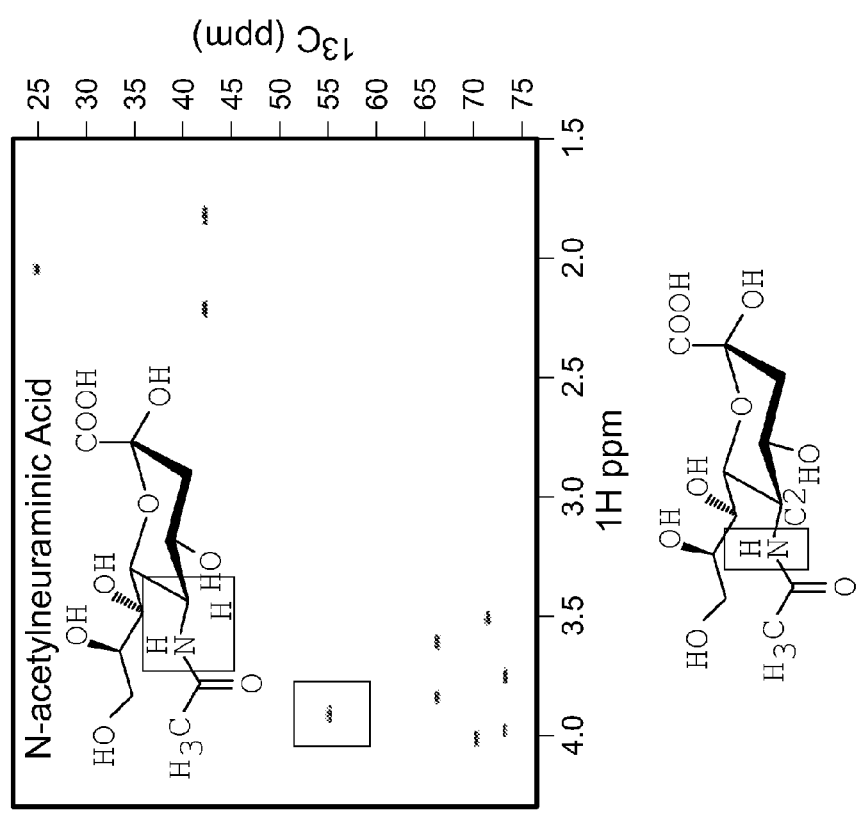
FIG. 8B
FIG. 8A

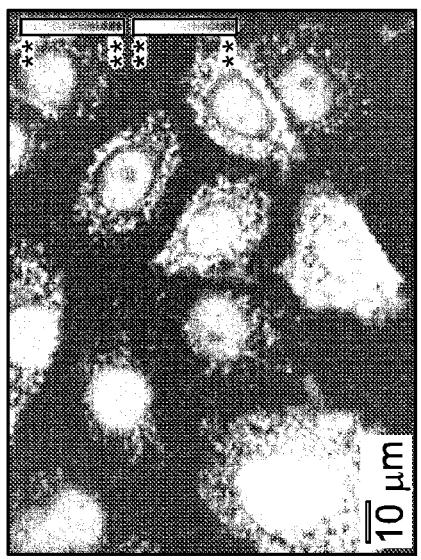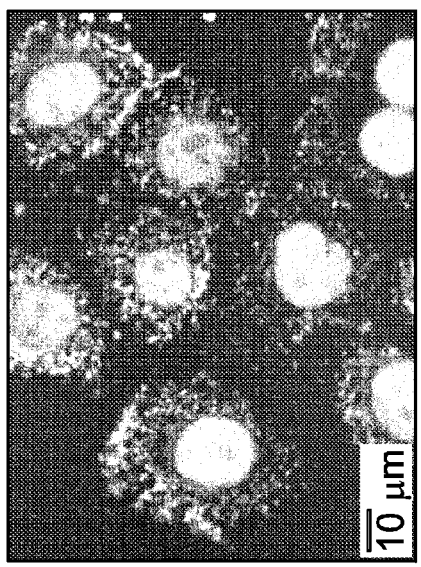
FIG. 9

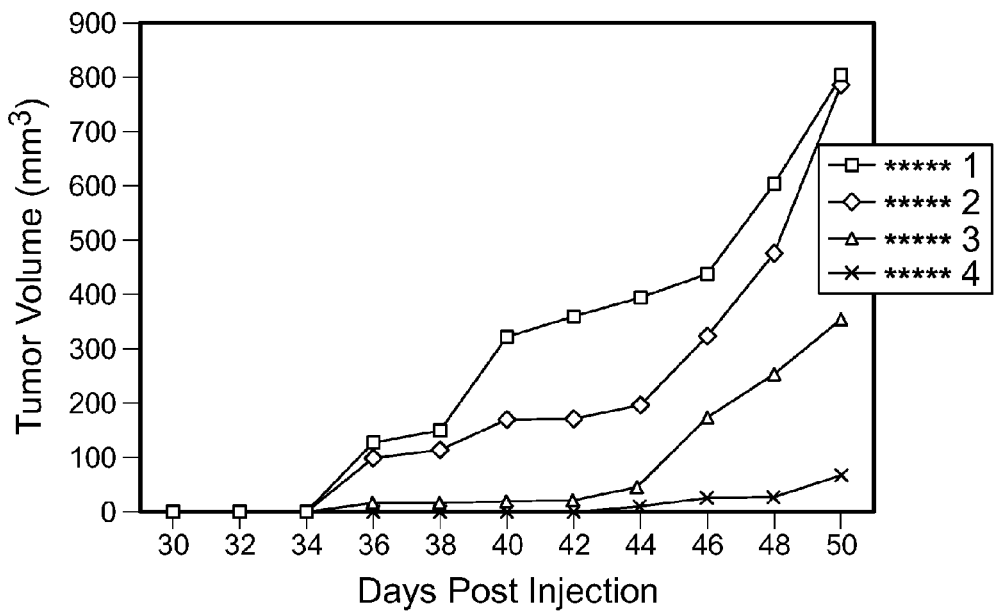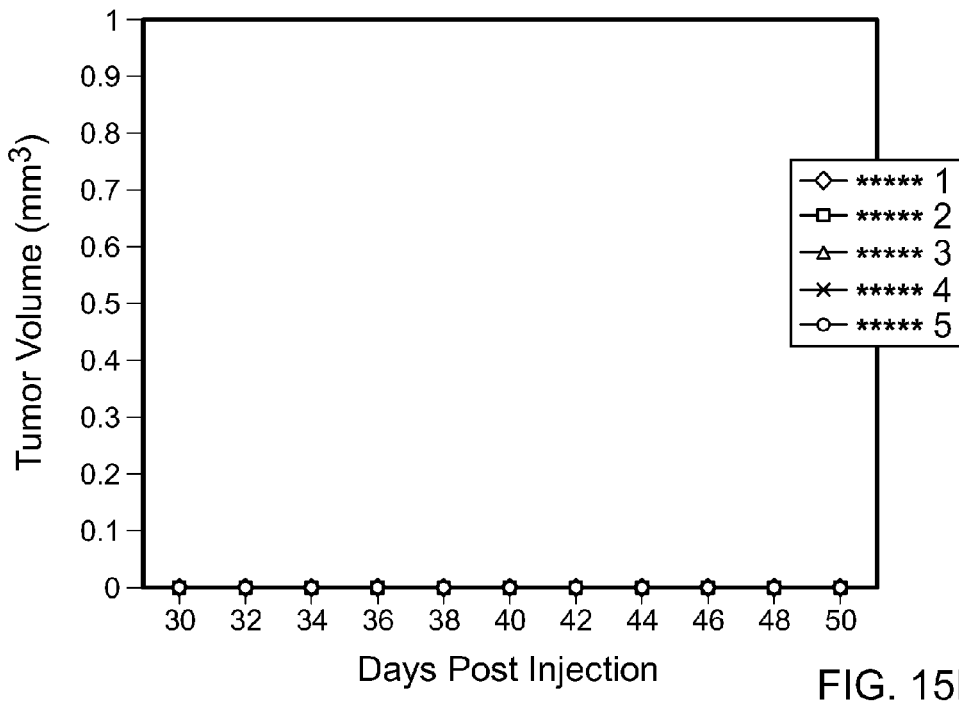
FIG. 15B

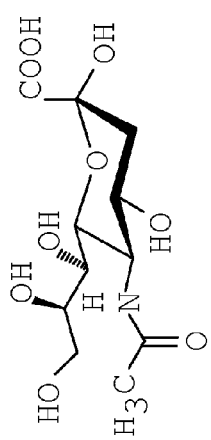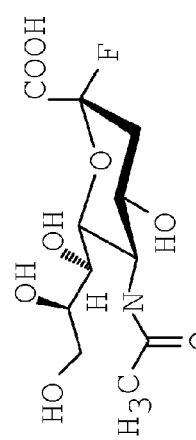
FIG. 16B
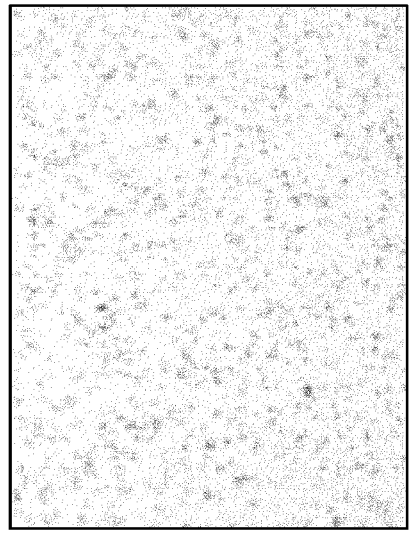
FIG. 16D
BPLER + F-NANA
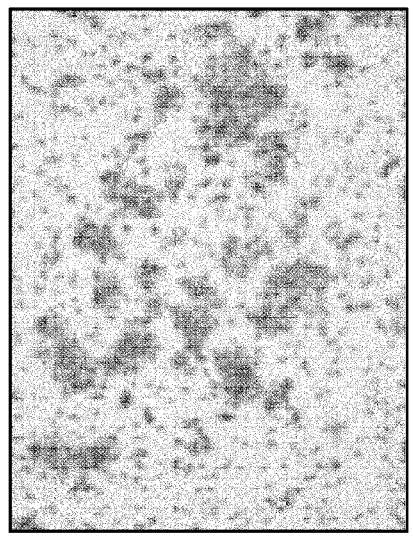
FIG. 16C
BPLER Relenza

BPLER

Tamiflu

BPLER- Relezna 1mg

NMR-BASED METABOLITE SCREENING PLATFORM

CLAIM OF PRIORITY

This application is a U.S. National Phase Application under 35 U.S.C. §371 of International Patent Application No. PCT/US2013/025628, filed on Feb. 11, 2013, which claims the benefit of U.S. Provisional Patent Application Ser. No. 61/597,298, filed on Feb. 10, 2012, the contents of both of which are incorporated herein by reference in their entirety.

STATEMENT AS TO FEDERALLY SPONSORED RESEARCH

The inventions were made with Government support under R21 AI087431 awarded by the National Institutes of Health. The government has certain rights in the inventions.

FIELD OF THE INVENTION

The invention relates to NMR-based screening platforms.

BACKGROUND OF THE INVENTION

The metabolic output of a cell is the summation of the functional genomic, transcriptomic and proteomic networks that define that cell type. Metabolomics is the comprehensive and simultaneous systematic determination of metabolite levels in the metabolome and their changes over time as a consequence of stimuli. While other fields may provide information, for example, regarding the copy number of a given gene, mRNA or protein; this study of chemical processes involving metabolites provides the downstream summation of all aberrant genes, RNAs, and/or proteins. This 'metabolic fingerprint' represents a snapshot of all the functioning or non-functioning pathways in a particular cell type.

Several analytical methods including mass spectrometry, chromatography, and NMR spectroscopy have been used to quantify cellular metabolites. Mass spectrometry and chromatography both require small sample amounts and can be easily adapted for high throughput analysis; however, both methods typically involve at least one if not several purification steps. Furthermore, in most cases the metabolites to be examined must be pre-selected a priori. Untargeted mass spectrometry approaches are possible but require several rounds of purification and further identification methods. In addition, not all metabolites, including nucleotide analogs and lipids, are easily ionizable and thus cannot be detected via mass spectrometry. Further, the fragmentation pattern resulting from mass spectrometry is not always suitable to distinguish between molecules such as sugars that have equal mass, but different structures, hence limiting the analysis.

SUMMARY OF THE INVENTION

Described herein is a rapid, unbiased, ultra-high resolution, quantitative NMR screening platform that utilizes any one, two, three, four, or all five, in any combination, of the following techniques: stable isotope labeling of a substrate, spectral width folding, random phase sampling, non-uniform sampling, and data extension for enhanced dynamic range data reconstruction, to generate custom "NMR Metabolite Arrays" in which the resonances of all known metabolites of a given cell sample are categorized and used for comparison for simplified statistical analysis. This is the first time all these techniques have been combined to provide a robust, efficient and high throughput NMR metabolite screening protocol. The combinations of steps allow for global, unbiased, ultra-high resolution of both water-soluble and lipid-based metabolites. In addition, the novel "NMR Metabolite Array" programs described herein provide a new way to analyze large complex NMR datasets in a simplified manner. The new platform permits both the rapid identification of differentially expressed metabolites, quantification of specific metabolites, and the ability to analyze the metabolic flux of given precursors.

The new methods enable one to specifically follow the metabolic breakdown of a particular molecule in relatively few cells, e.g., about 2-20 million cells. The methods involve preloading cells with a labeled precursor substrate (e.g., labeled with $^{13}C$, or $^{15}N$, or $^{31}P$) and using multidimensional NMR. The methods do not require purification of the individual metabolites of interest prior to analysis allowing for global, unbiased identification of metabolites that are differentially generated in cells with different properties.

Identification of metabolites differentially expressed in normal and disease state cells can be a powerful tool in the clinic. The new methods for monitoring differential expression of metabolites from cells that are phenotypically different are particularly useful for identifying therapeutic targets that can be used to modulate the phenotype. This includes targets that are present in the biosynthetic pathway of the metabolite, or the metabolite itself. Further, identifying differentially expressed metabolites can be used to differentiate cells of a normal versus a disease state. Hence, they have the potential to serve as a biomarker for the phenotype with which it is associated, making the methods described herein useful for identifying diagnostic markers, e.g., markers for diagnosis of disease.

For example, described herein we identified N-acetylneuraminic acid (NANA) as a novel biomarker for breast cancer tumor initiating cells, and monitoring its expression could be useful in diagnosing and detecting breast cancer. In addition, the protein level of CMAS, an enzyme in NANA biosynthesis was shown to be dramatically over-expressed in breast tumor initiating cells. Before this work, the role of CMAS in tumor initiation and metastasis has not been explored. Herein we provide evidence that CMAS expression is absolutely crucial for tumor formation and migration and that CMAS is a novel bona fide target for breast cancer.

The application of this methodology to an individual patient's cell analysis will also provide the basis for a "personalized medicine" approach to patient care.

Accordingly, this disclosure describes methods for monitoring the metabolism of a given substrate precursor within a cell population, e.g., a primary cell population, a tissue cell population, or cultured cells (e.g., immortalized cells). Using the methods described herein, the identification of differentially expressed metabolites between two or more cell populations that have different phenotypes is described. Also described are methods for identifying potential therapeutic targets and diagnostic markers.

In general, in a first aspect, the disclosure features new methods of monitoring metabolism of a substrate within a given type of cell in a sample. The new methods include (a) culturing a given type of cell of a first sample with a substrate for a sufficient period of time to allow metabolic breakdown of the substrate into substrate metabolites, wherein at least a portion of the substrate is optionally labeled with a nuclear magnetic resonance (NMR) stable isotope; (b) harvesting the substrate metabolites from the cells of step (a) to obtain a second sample of substrate metabolites; and (c) performing multi-dimensional NMR on the second sample of step (b) to determine a resonance spectrum of the metabolized substrate, wherein the resonance spectrum represents the metabolites of the substrate, and wherein the multi-dimensional NMR comprises any one of the following techniques: spectral width folding, random phase sampling, non-uniform sampling, and data extension for enhanced dynamic range data reconstruction.

In another aspect, the disclosure features methods for identifying differentially expressed substrate metabolites between a first population of cells and a second population of cells. These methods include (a) optionally loading a first and a second population of cells with a nuclear magnetic resonance (NMR) stable isotope-labeled substrate; (b) culturing the first and the second population of cells of step (a) for a sufficient period of time to allow metabolic breakdown of the substrate into substrate metabolites; (c) harvesting the substrate metabolites from the first and the second population cells of step (b) to obtain a sample of substrate metabolites from each of the first and the second cell populations; (d) performing multi-dimensional NMR on the sample of step (c) for each of the first and the second cell populations to determine a resonance spectrum of the metabolized substrate of the first population of cells and of the second population of cells, wherein the resonance spectrum represents the metabolites of the substrate; and (e) comparing the resonance spectrum of the first population of cells with the resonance spectrum of the second population of cells to determine which resonances are differentially expressed, wherein the differentially expressed resonances provide a resonance signature that represents differentially expressed metabolites.

In any of these methods, the multi-dimensional NMR can include any two, three, or all four, in any combination, of the following techniques: spectral width folding, random phase sampling, non-uniform sampling, and data extension for enhanced dynamic range data reconstruction. In any of these methods, the substrate can be labeled with an NMR stable isotope and the multi-dimensional NMR can include any two, three, or all four, in any combination, of the following techniques: spectral width folding, random phase sampling, non-uniform sampling, and data extension for enhanced dynamic range data reconstruction.

In some implementations of these methods, the substrate metabolites that are present in the sample are not purified away from the other molecules in the sample. In some implementations the substrate concentration within the population of cells is reduced for a period of time prior to loading the cells with the NMR-labeled substrate and the resonances of the metabolites of the labeled substrate are determined using NMR pulse programs or filtering techniques, or both, customized to the substrate. The number of cells within the population of cells can be is less than $2 \times 10^6$ and the population of cells can be a primary population of cells.

Any of these methods can further include comparing the resonance signature of step (e) with a database of known resonance signatures to determine the molecular structure that the resonance signature represents, and thereby determine the substrate metabolites that are differentially expressed between the first and the second populations of cells.

In certain implementations, the methods can further include identifying a biosynthetic pathway involved in generation of the substrate metabolites and identifying proteins/enzymes of the pathway that may be targeted to modulate the differential expression of the metabolite, to thereby modulate the phenotype of the cells. In some embodiments the first population of cells and the second population of cells are isogenic populations and/or the first population of cells and the second population of cells have different phenotypes. In some implementations, the first population of cells is a control population of cells and the second population of cells has been contacted with a test compound or agent. The methods can be used to identify metabolic pathways that are overactive or underactive in a particular cell type. The methods can further include inhibiting or overexpressing a gene in the second population of cells and the method is used to identify the metabolic consequences of over-expressing or inhibiting a gene in a cell.

In another aspect, the disclosure features methods for treating cancer in a subject. The methods are based on results determined using the new platform methods described herein. The methods of treating cancer include administering to a subject in need thereof an effective amount of an inhibitor of N-acylneuraminate cytidylyltransferase (CMAS), an inhibitor of N-acetylneuraminic acid synthase (NANS), or a molecule that decreases the expression of N-acetylneuraminic acid. For example, the inhibitor can be an enzyme or can be selected from the group consisting of a small molecule, a ribonucleic acid, a deoxyribonucleic acid, a protein, a peptide, and an antibody.

As used herein, the term "isogenic" refers to cells of the same genetic background (any cell type, e.g., epithelial, or fat, or stem, or muscle cells etc.) that are isolated from the same tissue type (any tissue, e.g., tissue of the same organ, skin, bladder, liver, heart, etc.) and from the same organism type (e.g., human, or animal, or fish).

As used herein, the term "metabolite" refers to the intermediate or the end products of metabolism. "Metabolites" have functions comprising energy source, structural, signaling, stimulatory, and inhibitory effects on enzymes. Metabolites can also have catalytic activity themselves. A metabolite can be the end product of a substrate-enzyme reaction.

As used herein, the term "metabolic precursor" is a compound that participates in a chemical reaction. The term is meant to include to a compound that is a starting compound or an intermediate compound of an enzymatic reaction from which an end product results.

The term "substrate" refers to a molecule or compound on which an enzyme acts and results in the substrate transforming into one or more end products. The end products are released from the active site of the enzyme.

The term "enzyme" refers to a molecule that accepts a substrate in its active site and transforms the substrate into one or more end products that are subsequently released from the active site.

As used herein, the term "primary cell" or "primary tissue" refers to cells or tissue taken directly from living tissue of a normal individual or an individual with an acquired or inherited disease and established to grow in vitro.

The term "metastasis" refers to a process by which cancer spreads from the place at which it first arose as a primary tumor to distant locations in the body as well as the newly established tumor itself, which is also referred to as a "metastatic tumor" that can arise from a multitude of primary tumor types, including but not limited to those of prostate, colon, lung, breast, bone, and liver origin. Metastases develop, e.g., when tumor cells shed from a primary tumor adhere to vascular endothelium, penetrate into surrounding tissues, and grow to form independent tumors at sites separate from a primary tumor.

The term "cancer" refers to cells having the capacity for autonomous growth. Examples include cells having an abnormal state or condition characterized by rapidly proliferating cell growth. The term is meant to include cancerous growths, e.g., tumors (e.g., solid tumors); oncogenic processes, metastatic tissues, and malignantly transformed cells, tissues, or organs, irrespective of histopathologic type or stage of invasiveness. Also included are malignancies of the various organ systems, such as respiratory, cardiovascular, renal, reproductive, hematological, neurological, hepatic, gastrointestinal, and endocrine systems; as well as adenocarcinomas which include malignancies such as most colon cancers, renal-cell carcinoma, prostate cancer and/or testicular tumors, non-small cell carcinoma of the lung, cancer of the small intestine, and cancer of the esophagus. Cancer that is "naturally arising" includes any cancer that is not experimentally induced by implantation of cancer cells into a subject, and includes, for example, spontaneously arising cancer, cancer caused by exposure of a patient to a carcinogen(s), cancer resulting from insertion of a transgenic oncogene or knockout of a tumor suppressor gene, and cancer caused by infections, e.g., viral infections. The term "carcinoma" is art recognized and refers to malignancies of epithelial or endocrine tissues. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures.

As used herein, the term "treating" or "treatment" refers to administering one or more of the compounds described herein to a subject who has an a disorder treatable with such compounds, and/or a symptom of such a disorder, and/or a predisposition toward such a disorder, with the purpose to confer a therapeutic effect, e.g., to cure, relieve, alter, affect, ameliorate, or reduce the disorder, the symptom of it, or the predisposition.

As used herein, the term "an effective amount" or "an amount effective" refers to the amount of an active compound that is required to confer a therapeutic effect on the treated patient. Effective doses will vary, as recognized by those skilled in the art, depending on the types of diseases treated, route of administration, excipient usage, and the possibility of co-usage with other therapeutic treatment.

Dosage, toxicity, and therapeutic efficacy of therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the inventions will be apparent from the following detailed description, and from the claims.

BRIEF DESCRIPTION OF THE DRAWINGS

FIGS. 2A-2D demonstrate spectral width (sw) folding strategies, in which decreasing the sw from 220 pm to 90 ppm led to 2.5 fold increase in resolution. FIG. 2E summarizes a non-uniform sampling (NUS) strategy allowing either an 8-fold increase in resolution or a 4-fold increase in resolution in time reduction by 40%. FIG. 2F shows a NUS 13C-1H HSQC spectra (left) processed using forward maximum entropy reconstruction and the same NUS 13C-1H HSQC spectra (right) after including a data-extension step in the reconstruction that increased resolution by 2-fold.

FIGS. 3A and 3B are $^{13}C$-$^{1}H$ HSQC spectra indicating the full metabolic coverage of water-soluble (3A) and lipid-based (3B) metabolites from the same p53 deficient mouse lung tumor, respectively.

FIGS. 7A-B are representative examples of $^{13}C$-$^{1}H$ HSQC resonance spectra of water soluble glucose derived metabolites in breast tumor initiating BPLER cells (FIG. 7A) and less malignant isogenic HMLER cells (FIG. 7B).

FIG. 7C summarizes the NMR arrays for the BPLER and HMLER $^{13}C$-$^{1}H$ HSQC resonance spectra, showing how the intensity (Y-axis) of all possible metabolite resonances (X-axis) changes in each cell type. BPLER and HMLER cells originate from the same normal breast tissue and were grown into two cell types BPECs (breast primary epithelial cells) grown in chemically defined WIT medium and HMECs (human mammary epithelial cells) grown in MEGM media. BPEC and HMEC cells were transformed with hTERT (L), the SV40 early region (E), and H-ras (R) to give rise to BPLER and HMLER cells.

FIG. 7D is a zoomed in region of the a overlay of BPLER (red) and HMLER (blue) $^{13}C$-$^{1}H$ HSQC spectra in a region the NMR array predicted to only have BPLER resonances.

FIGS. 8A-C summarize various methods used to validate that the differentially expressed metabolite overexpressed in the BPLER NMR arrays is N-acetylneuraminic acid (NANA). FIG. 8A is the $^{13}C$-$^{1}H$ HSQC of pure NANA. FIG. 8B illustrates the results of custom NMR HCN (hydrogen-carbon-nitrogen) experiment, confirming BPLER cells have a differentially expressed resonance with similar connectivity to NANA. FIG. 8C shows the M/S results directly measuring NANA in HMLER (left) and BPLER (right) cells using liquid chromatography-mass spectrometry multiple reaction monitoring (LC/MS MRM) where the number reported is the area under the NANA peak.

FIG. 9 is a series of representations of microscope images of rhodamine-labeled wheat germ agglutinin (WGA) immune-fluorescent microscopy showing the expression of NANA in HMLER (top row) and BPLER cells (bottom row), respectively. WGA specifically binds to NANA.

FIGS. 12A and 12B are each a series of immunohistochemistry images showing the inhibition of cell migration in the absence of NANS and CMAS and the rescue of migration with NANA in HMLER and BPLER cells, respectively. FIG. 12C is a bar graph quantifying the number of migrating cells in the absence of NANS and CMAS and the subsequent migration following addition of NANS.

FIG. 14A is a series of immunohistochemistry images of HMLER cell migration following overexpression of CMAS. FIG. 14B is a series of immunohistochemistry images of BPLER cells and with stable CMAS knockdown BPLER cells (BPLER-shCMAS1).

FIGS. 15A-B summarize the strategy to determine the effect of CMAS levels on tumor initiation and metastasis in vivo. FIG. 15A shows the immunization scheme, and FIG. 15B shows the tumor volume growth per day after in NOD/SCIN mice injected with 500,000 BPLER (left) or 500,000 BPLER-shCMAS1 cells.

FIGS. 16A, 16B, 16C, and 16D are the enzyme mechanism of CMAS, a synthesized substrate based inhibitor of CMAS based on the structure of NANA, and immunohistochemistry analysis showing the inhibition of cell migration with the synthesized fluorine-NANA inhibitor, respectively.

DETAILED DESCRIPTION

Figure 1:
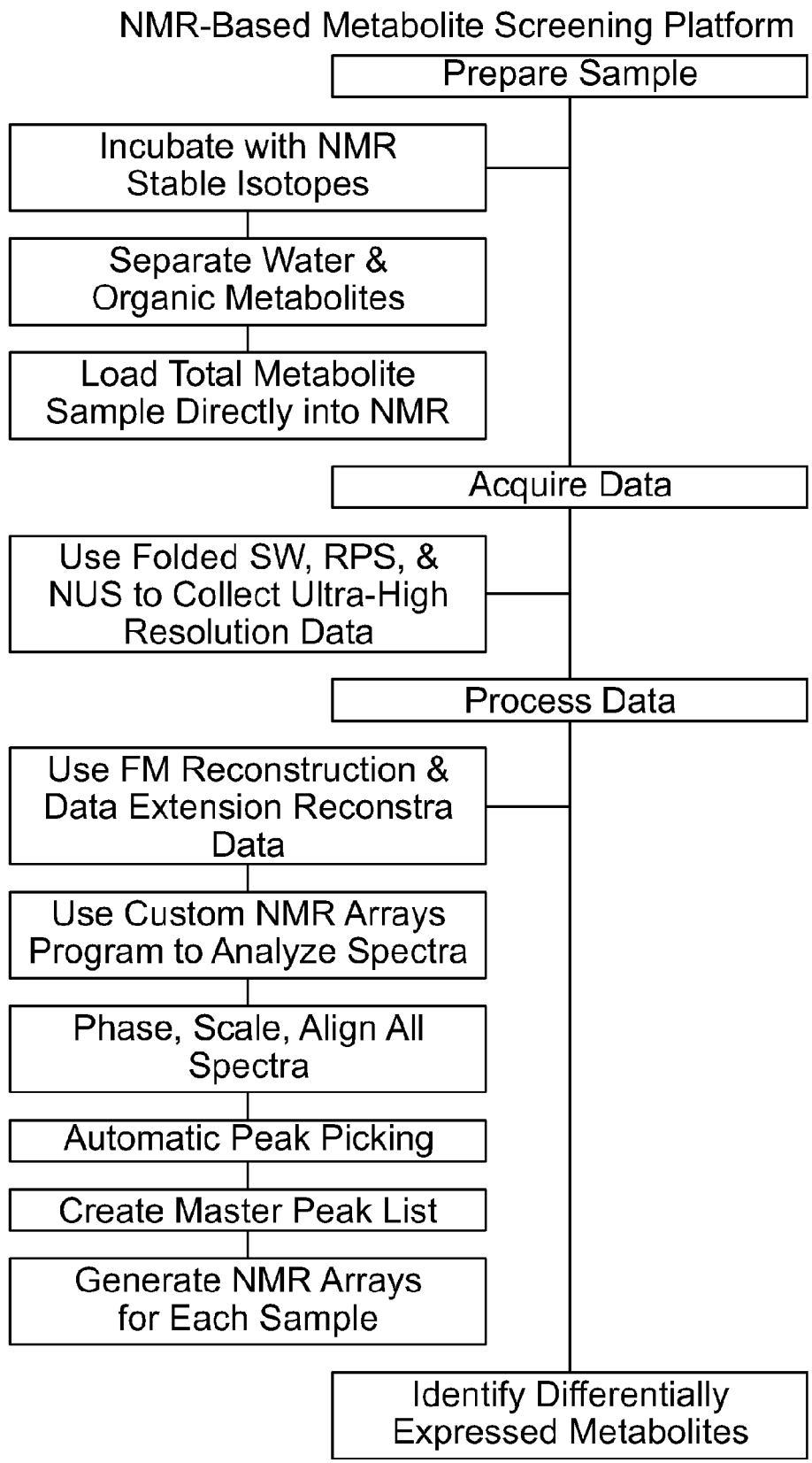
FIG. 1 is a flow chart summarizing the key steps of the NMR based metabolite screening platform described herein.

The present disclosure describes novel methods that provide benefits over numerous aspects of known NMR data acquisition and allow for rapid, unbiased, global, quantitative ultra-high resolution NMR data acquisition and custom NMR analysis utilizing a novel approach. The present disclosure describes new NMR screening methods that can be used to identify, follow, and characterize the metabolic breakdown of a particular molecule and to analyze the cellular metabolomics essential to a given cell type. The methods described herein circumvent the hurdles presented by known NMR protocols, namely a reduction in the sample size necessary to perform the data acquisition, eliminating the need for purification of the metabolites to be analyzed, reduced experimental time required for multi-dimensional NMR and obtaining high resolution necessary for metabolite identification. The method requires relatively few cells (2-20 million), allowing the methods to be used to study metabolites from primary cells and tissues rather than just from cell cultures. In addition, the disclosed methods do not require purification of the individual metabolites of interest from other cellular metabolites prior to analysis. Further, the new methods allow one to visualize the specific metabolic fate of a given precursor in any cell type, and thus provide for the simplified identification of metabolites that are differentially generated in different types of cells utilizing novel data analysis methods also described herein.

To highlight the power and breadth of the new platform methods, this disclosure describes the identification of differentially expressed metabolites in triple negative breast cancer tumor-initiating BPLER cells that are highly aggressive compared to a less malignant isogenic line HMLER. It is widely known in the field that cancer cells thrive on glucose consumption. The glucose metabolite N-acetylneuraminic acid (NANA) has been identified herein as being differentially expressed in breast cancer tumor-initiating BPLER cells (i.e., increased expression). The biosynthetic pathway that generates the metabolite has also been identified and used to identify proteins/enzymes required for the synthesis of the metabolite as candidate targets within the pathway to modulate the phenotype of increased tumor initiation and metastatic potential.

In addition, the results of knock-down experiments in which genes that produce key enzymes NANS and CMAS are silenced demonstrated that the reduction of the normal function of these enzymes to generate NANA and attach it to proteins had no effect on the proliferation of BPLER cells, but greatly reduced their migration. On the other hand, forced over-expression of the same enzymes in HMLER cells increased their migration. Stable knockdown of CMAS in BPLER cells completely prevented tumor formation in mice. Thus, the new methods were successfully used to identify metabolites (e.g., NANA) important for tumorigenicity and to demonstrate that NANA and the proteins involved in the synthesis of NANA may serve as targets for therapeutic intervention to reduce breast tumor formation and the metastasis of tumor-initiating cells. In addition, NANS, and CMAS were validated as targets for inhibition of tumor initiation and metastasis in vitro and in vivo. Thus, small molecule and other inhibitors of these enzymes are new candidate therapeutic agents that can be used to specifically target breast tumor-initiating cells. Furthermore, the differentially expressed metabolites (e.g., NANA) can also serve as biomarkers for the phenotype with which they are associated, allowing the methods described herein to be used to identify new candidate diagnostic markers.

General Methodology

In general, the new methods described herein for monitoring metabolites of a given precursor molecule (i.e., substrate) within a given type of cell include the steps of: (a) optionally loading a population of cells with a labeled substrate, e.g., a $^{13}$C-labeled substrate, (b) culturing the cells of step (a) for a sufficient period of time to allow metabolic breakdown of the substrate into substrate metabolites (e.g., typically 5 minutes to 24 hours depending on the experimental question); (c) harvesting the substrate metabolites from the cells to obtain a sample of substrate metabolites, e.g., a water-soluble sample of substrate metabolites and organic sample of lipid-based metabolites; and (d) performing multi-dimensional NMR on the sample of step (c) to determine the resonance spectra of the metabolized substrate, wherein the resonances represents the resonances of metabolites of the substrate. How the multi-dimensional NMR is performed is described in further detail below.

In these methods, various substrates and various stable spin-½ nuclear isotopes can be used to label those substrates. For example, glucose, glutamine, fatty acids, amino acids, pyruvate, drug compounds, and other molecules can be used as substrates, and stable isotopes such as $^{13}$C, $^{15}$N, $^{29}$Si, $^{31}$P, or others can be used to label the substrates. Any tissue, primary cells or cultured cell lines can be used for the analysis, such as cancer cells, muscle cells, fat cells, endothelial cells, epithelial cells, neuronal cells, cardiac cells, and many others. In general, one would want to test cells associated with a particular disease or disorder, such as a cancer cell, as well as the same type of cells from a healthy subject, to provide a differential metabolic analysis. One could also test cells with a single gene mutation (i.e. mutant cells vs. wild-type) or cells treated or not with a drug, or the same cells incubated with the precursor for various times. The cell populations of each sample can be a homogeneous cell population. In alternative embodiments, the cell population of each sample can be a heterogeneous cell population (e.g., derived from a tissue sample). While any number of cells can be used in the methods described herein, in various embodiments the number of cells within each population of cells can be less than $1\times10^8$, less than $8\times10^7$, less than $7\times10^{7'}$, less than $6\times10^7$, less than $5\times10^7$, less than $2.5\times10^7$, or less than $2.0\times10^7$, or the cell number can range from approximately $1\times10^6$ to $1\times10^8$ cells, or $1\times10^6$ to $5\times10^7$, or $1\times10^6$ to $2.5\times10^7$, or $1\times10^6$ to $2.0\times10^7$.

Methods for loading cells are well known to those of skill in the art, e.g., the labeled substrate can be added to the cell culture medium for a period of time (e.g., 5 minutes to 24 hours), or may be loaded by transfection (e.g., liposome or calcium phosphate), transduction (e.g., viral delivery of labeled substrate) or transfusion (e.g. direct injection into a tumor). In one embodiment, labeled precursor is administered to a subject, e.g., orally, topically, parenterally, or intravenously. In some embodiments, the labeled substrate is added to animal feed.

In various embodiments, prior to adding the culture medium containing the labeled substrate, the cells are incubated with cell culture medium that lacks any form of the substrate, e.g., lacks the substrate in unlabeled or labeled form. The cells may be incubated in this medium for minutes to hours, essentially starving the cells of the substrate. This helps reduce background in the later analysis. The cells are then incubated with cell culture medium containing only labeled substrate, (e.g., 5 minutes to 24 hours). Any concentration of substrate can be used. In various embodiments, the concentration ranges from 1 ng/ml to >1 mg/ml. A skilled artisan can easily determine the best concentration to use by testing various concentration ranges. After incubation the cells are washed briefly and immediately harvested to separate the metabolites. To harvest the metabolites, a simple chloroform extraction may be performed in order to obtain a water-soluble sample or a non-water soluble sample of metabolites present in the organic layer. No additional purification is required.

Several nuclear magnetic resonance (NMR) techniques may be used in the methods of the invention, preferably multidimensional NMR. For example, heteronuclear single quantum correlation (HSQC) spectroscopy, variations of HSQC, and other multidimensional NMR techniques can be used. Methods for performing multidimensional NMR (e.g., 2D NMR and/or $^{13}$C-$^{1}$H HSQC NMR) are well known to those of skill in the art.

The resonance spectra of the metabolites of the labeled substrate can be determined using NMR pulse programs, which can be customized to the substrate. In general, NMR uses a static, homogeneous external magnetic field to polarize the NMR sample. This primary field is typically called the "B0" field, and it defines a reference axis for the NMR system. The NMR sample is magnetized in the direction of the B0 field by placing the sample in the B0 field for a period of time (e.g., minutes) and allowing the sample to reach a thermal equilibrium state. The primary B0 field also typically defines the resonance frequencies of the spin-½ nuclear species in the sample. For example, a stronger primary field generally increases the nuclear spins' resonance frequencies. The nuclear spins "precess" about the B0 field at their respective resonance frequencies. In most NMR systems, the nuclear spins have a resonance frequency in the radio frequency (rf) range.

In NMR experiments, the nuclear spins in the NMR sample are manipulated by applying a time-varying magnetic field at the nuclear spins' resonance frequency. In some instances (e.g., for low flip-angle pulses), high-intensity radio frequency (RF) pulses provide fast, precise control of the nuclear spins. High-intensity RF pulses have the benefit of shorter pulse times, which reduces the amount of decoherence that occurs during the pulse. In some instances (e.g., for high-flip angle pulses), high-intensity RF pulses provide less precision, for example, due to non-uniform power output over a frequency range of interest, due to spatial inhomogeneity in the RF field, or due to other considerations.

In some implementations, adiabatic pulses can provide more precise control of the nuclear spins. Adiabatic pulses typically have a lower intensity and require a longer pulse time. In some cases, adiabatic pulses are used for larger flip-angle pulses (e.g., 180 degree flip angle) to provide a more uniform flip angle over the entire frequency range of interest. Adiabatic pulses are typically implemented shaped pulses (meaning that they have a time-varying power profile) that can be parameterized for a particular flip angle, a particular frequency range, etc.

In various embodiments, the new NMR methods include the use of any one or more the following methods and techniques to increase analysis speed and/or resolution, or both: (i) stable isotope labeling (ii) folding the spectra width and aliasing peaks, (iii) random phase sampling (iv) non-uniform sampling, and (v) data extension. In some embodiments the methods include at least two or three of these methods in any combination. In some embodiments, the methods include all five methods. Table 1 below summarizes the effects of each step on the NMR acquisition and data resolution. These steps are described in more detail below.

TABLE 1

| METHOD | EFFECT ON NMR ACQUISITION & DATA RESOLUTION |
| --- | --- |
| Stable isotope labeling | Increases metabolite signal detection by 99% |
| Folding spectral width (sw) | Increases resolution by 2.5 fold to 44 Hz (approaching theoretical limit of C-C decoupling) |
| Random phase sampling | Decreases the total acquisition time by 50% |
| Non-uniform sampling | For time equivalent spectra one can gain 8-fold increase in resolution or one can gain 4-fold increase in resolution and at the same time cut experimental time by 40%. |
| Data-extension | 2-fold increase in data resolution with no effect on experimental time |

Stable Isotope Labeling

Traditional 2-D NMR metabolite profiling relies on $^{13}$C-natural abundance, which exists at 1.1%. As such, in order to observe any signal at all, large amounts of sample are required (on the average +200 million cells). This limits detection to cultured cells lines and only the most abundant metabolites are detected. To decrease the amount of material needed and view metabolites with a broader concentration range, samples (e.g., cells, tissues or tumors) were directly supplemented with $^{13}$C-labeled precursors (glucose, glutamine, pyruvate and amino acids were used but other substrates and other isotopes are also possible). Theoretically, this should decrease the sample burden by ~99%. If, for example a 1 mM metabolite required 200 million cells to be detected with $^{13}$C natural abundance, using a label to see the same intensity would require only 2 million cells. Including this step in our method reduces sample requirements to those similar for some mass spectrometry (M/S) approaches. Untargeted M/S requires at least 1 million cells and is followed by several rounds of chromatography purification and detection. Our method requires few cell numbers and no purification.

Folding the Spectra Width and Aliasing Peaks

When an atom is placed in a strong magnetic field (B0), the electrons in that molecule precess in the direction of the applied magnetic field. This precession creates a small magnetic field at the atomic nucleus. The magnetic field at the nucleus (B) is therefore generally less than the external magnetic field (B0) by τ.

$$B = B0(1-\tau).$$

The electron density around each nucleus within a molecule varies according to the types of nuclei and the bonds in the molecule. The opposing field and therefore the effective magnetic field at each nucleus will vary. In pulsed NMR spectroscopy these differences can be measured by applying a radio frequency pulse that causes the nuclear magnetization to oscillate inducing an electrical current in a coil that can be measured. This signal, known as "free induction decay" (FID) is plotted as current with respect to time. By applying a discrete Fourier transform, the FID can be converted to frequency domain and the resonance frequency of each observable nuclei can be converted to chemical shift (δ) by the equation, $$\delta = (n - n_{REF}) \times 10^{-6} / n_{REF}$$

where n is the resonance frequency of the nucleus and $n_{REF}$ is the resonance frequency of a standard.

Chemical shift is a very precise metric of the chemical environment around a nucleus. Unlike M/S and chromatography, NMR is one of the only methods that can distinguish molecules that have the same mass but different chemical connectivity. However to utilize this information ultra-high resolution spectroscopy is needed.

In NMR, digital resolution is determined by the sweep width (sw) and the total number of data points (TD), such that $$\text{Resolution} = sw/TD, \text{measured in Hz/point}.$$

SW is the range of frequencies over which NMR signals are to be detected. Metabolite mixtures contain diverse molecules, and the spectral width necessary to cover all potential carbon chemical shifts spans over –220 ppm. The large $^{13}$C-chemical shift window creates a dilemma, where in order to have maximum resolution and a broad enough sw to encompass all possible chemical shifts one would require an incredibly large number of data points. In practical terms this is time-prohibitive.

To circumvent this, our method can include folding the sw. The sw is purposefully set to smaller range and if some peaks occur outside this range they will appear "folded" at aliased chemical shifts. Folded spectra can be unfolded by suitable data processing techniques. For example, resonance frequencies can be dealiased by expanding the frequency spectrum and shifting the aliased frequencies by a predefined amount, to their actual locations. In some cases, the data acquisition parameters define the spectral folding windows in a manner that reduces or minimizes any overlap between folded spectral peaks and non-folded spectral peaks. As such, the folded spectral peaks can be de-aliased without affecting other data in the frequency spectrum, in some cases. Folding spectra decreases the overall number of points required in order to achieve the maximum resolution possible. Our custom folding strategy and de-aliasing program allows ultra-high resolution spectra with ~44 Hz/point separation.

Random Phase Sampling

As described above converting the FID signal to frequency data requires Fourier transformation. However, for a nuclei rotating at +x magnetization vector around the Z-axis, the Fourier transform will give peaks at both +v and –v because the Fourier transformation cannot distinguish between a +v and –v rotation of the vector. The most common method to distinguish the sign of the frequency requires sampling the signal at two different receiver phases (for example 0° and 90°). For multidimensional NMR this increases the experiment time by a factor of two for each dimension. To increase the speed of our analysis we employed random phase sampling (RPS) where a single phase is used to detect each point but the phase is randomly alternated for different points in the signal. This allows us to resolve the phase of the frequency but cut the acquisition time in half.

Non-Uniform Sampling and Data Extension

Two-dimensional NMR techniques generate two dimensions of data in the time domain: a direct domain and an indirect domain. The direct domain data are generated by running an experiment and collecting an NMR signal (e.g., an FID, an echo, or a stroboscopic signal). In other words, the direct domain is the time domain of an NMR experiment. The indirect domain data are generated by systematically varying a time parameter of the NMR experiment (e.g., incrementing a delay time), running the NMR experiment for each value of the parameter, and combining the NMR signals from all experiments. In other words, the indirect domain is the time domain of the parameter that is systematically varied.

In some cases, non-uniform sampling can be used in multi-dimensional NMR for the methods described herein. For example, non-uniform sampling can be used in the indirect domain to reduce the number of NMR experiments that are needed to obtain a particular spectral range and frequency resolution.

Non-uniform sampling (NUS) can be accomplished by incrementing the indirect domain time parameter systematically and in a non-uniform manner. In particular, instead of incrementing the time parameter by the same amount for each successive NMR experiment, the time parameter can be incremented by an amount that varies depending on one or more factors. For example, the time delay parameter can be incremented by an amount that changes (e.g., increases or decreases) from experiment to experiment. Varying the time delay according to a Poissonian distribution or another nonlinear distribution results in sparsely sampled indirect domain data. The missing points in the "sparse" data set can be calculated using reconstruction methods. The forward maximum entropy reconstruction technique can conserve the measured time-domain data points and guess the missing data points by an iterative process. The iterative process can include discrete Fourier transformation of the sparse time-domain data set, computation of the spectral entropy, determination of a multidimensional entropy gradient, and calculation of new values for the missing time-domain data points with a conjugate gradient approach. Since this procedure does not alter measured data points, it can reproduce signal intensities with high fidelity and avoid dynamic range problems. In some cases, our method indicates with appropriate sampling schedules NUS has enhanced ability to detect weak peaks. This is extremely important for metabolite analysis where there is a large dynamic range between abundant metabolites (milimolar concentration) and rare metabolites (nanomolar concentration).

During the reconstruction it is possible to further increase the resolution of resonances utilizing "data extension." In this method, during the reconstruction, the total number of points in the indirect dimension is doubled. In one embodiment, the first half of the time domain (composed of NUS sampled points) is solved according to standard forward maximum entropy protocols and the second half of the data that does not contain any sampled points is completely built using iterative soft thresholding. In some cases, this allows a two-fold increase in resolution without affecting acquisition time.

Optional Enhancements to Reduce Background

In general, when using the methods described herein there is no need to purify or isolate the substrate metabolites that are present in the sample from the other molecules in the sample (e.g., by chromatographic column (e.g., Sidelmann, et al. Purification and 1H NMR Spectroscopic Characterization of Phase II Metabolites of Tolfenamic Acid Drug Metab Dispos Jun. 1, 1997 25:725-731) or by other means well known to those of skill in the art). Thus, in typical embodiments, the only purification performed in the method prior to NMR is the separation of the metabolites into a water soluble sample or a non-water soluble sample.

In some embodiments, the concentration of the unlabeled substrate within the cell can be reduced for a period of time (e.g., 10 minutes to 4 hours) before adding the labeled substrate. This technique can help reduce background signal.

The appropriate time frame can be determined by testing a range of conditions and monitoring background as compared to control cells not loaded with labeled substrate.

Automated NMR Analysis

Figure 4:
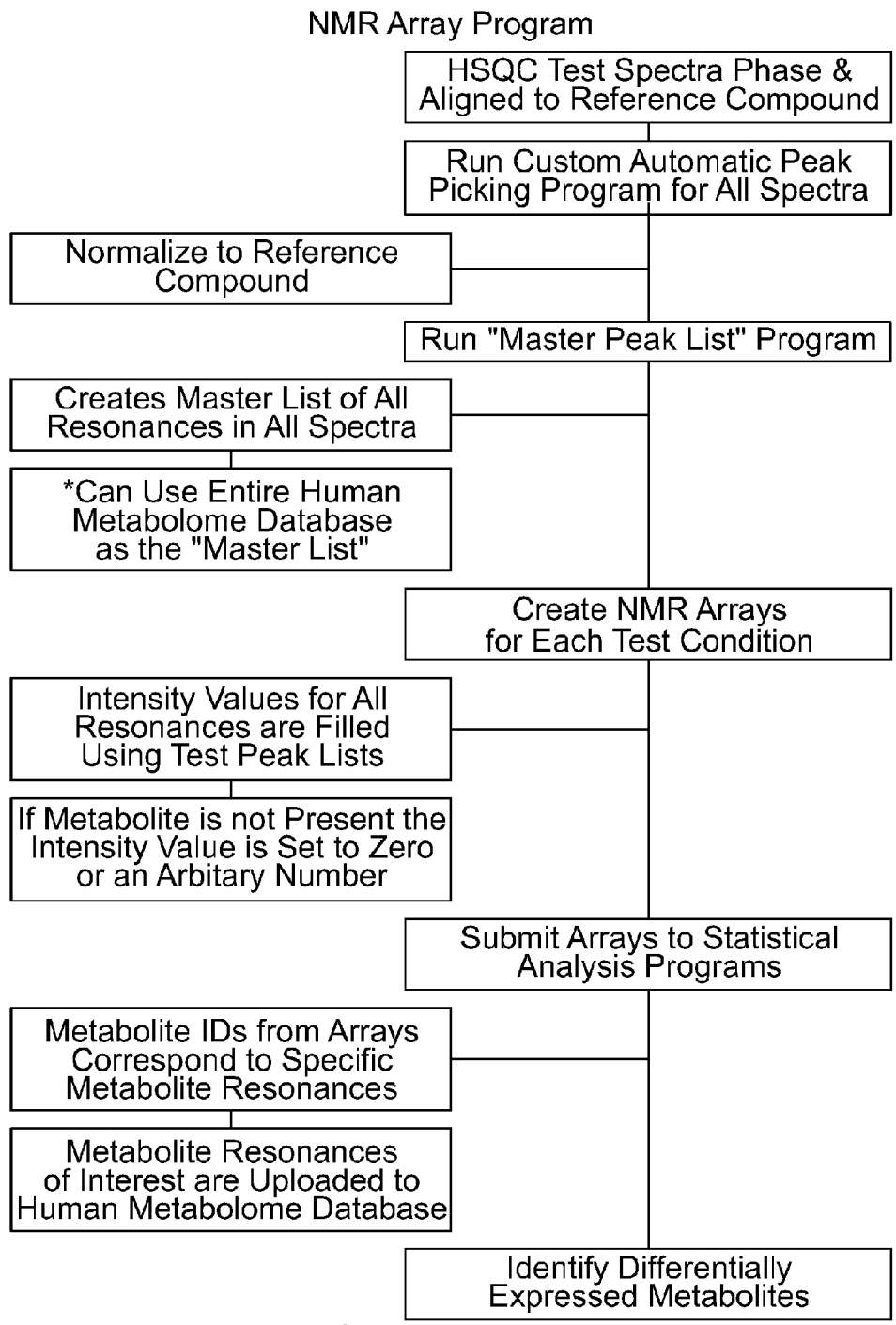
FIG. 4 is a flow chart summarizing the custom NMR analysis program used to create NMR arrays for rapid analysis.

NMR metabolite analysis is tedious and complex. To circumvent these problems, a custom "NMR Metabolite Arrays" program was created to automate the process. As shown in FIG. 4, spectra are automatically first phased, aligned, and normalized with a spike-in control. For example, a known material, such as 4,4-dimethyl-4-silapentane-1-sulfonic acid (DSS), tetramethylsilane (TMS), trimethylsilyl propionate (TSP), 4,4-dimethyl-4-silapentane-1-ammonium trifluoracetate (DSA) or other NMR standard reference compound can be added into each sample, and its concentration used as a reference to enable relative quantification comparisons between samples. Next, using a custom automatic peak picking program, peak lists can be generated for each sample, where each resonance peak is converted into an X, Y coordinate with an intensity value. A "MASTER PEAK LIST" program that generates a "master" look up table for all the resonances in the spectra under investigation can then be run. This program reads all X, Y points from the individual peak list files, removes duplicates within defined tolerances, and writes the resulting set of peaks to a standard output such that all possible metabolite resonances under investigation are determined. Depending on the analysis it is possible to input the entire HSQC data from the Human Metabolite Database into the master peak-list. However, taking this approach requires longer computation times, and in most cases is unnecessary. Thus, creating master look up tables for the spectra that are specifically being investigated is preferred.

As further shown in FIG. 4, after creating the master look up table, "NMR arrays" are next generated for each sample. NMR arrays consist of a list of all possible metabolites and intensity values for each resonance under investigation. They are created by combining the individual test peak list and master peak list to fill in the intensity for resonances for all possible metabolites. If a metabolite is expressed in a test sample, the program will select that intensity value. If it is not present, the intensity is set at zero or an arbitrary number. The NMR arrays can then be analyzed via traditional statistical analysis programs to identify the differentially expressed resonances between spectra. The resonance frequencies can then be uploaded directly into a database, such as the Human Metabolome Database, to identify which metabolites are differentially expressed. Candidate metabolites can then be confirmed via additional NMR or M/S experiments.

Differential Expression Analysis

Also provided herein are novel methods for identifying substrate metabolites differentially expressed by at least two populations of cells, e.g., a first population of cells and a second population of cells. One of the populations of cells can be from a healthy subject or cell line and used as a control. The methods can use the various features of the various method steps and techniques described herein and include: (a) loading a first and a second population of cells with a labeled substrate (e.g., a $^{13}C$, $^{15}N$, or $^{31}P$-labeled substrate); (b) culturing the first and the second population of cells of step a) for a sufficient period of time to allow metabolic breakdown of the labeled substrate into substrate metabolites; (c) harvesting the substrate metabolites from the first and the second population cells of step (b) to obtain a sample of substrate metabolites from each of the first and the second cell populations, (d) performing multidimensional NMR on the samples from each of the first and the second cell populations to determine the resonance spectra of the metabolized substrate, wherein the resonance spectra represents the metabolites of the substrate; and (e) processing the resonance spectra using a custom "NMR arrays" program (f) comparing the resonance intensity of the first population of cells with the resonance spectra of the second population of cells to determine which resonance spectra are differentially expressed, wherein the differentially expressed resonance spectra represents differentially expressed metabolites.

In some embodiments, the methods for identifying differentially expressed substrate metabolites between at least two populations of cells can further include comparing the resonance spectra of step (f) with a data base of known resonance spectra to determine the molecular structure(s) that the resonance spectra represents, and thereby determine which specific substrate metabolites are differentially expressed between the first and second, different population of cells. Specific metabolites may be identified in this manner.

The methods described herein are useful for monitoring metabolism in any cell type, as well as in any tissue (e.g., the cell population can contain a heterogeneous population of cells), and are useful for monitoring metabolism in cells exhibiting any phenotype as compared to a cell not exhibiting the phenotype.

Diagnostic Applications

Identified differentially expressed metabolites are indicative of the different phenotype, and their expression can therefore be used to diagnose this phenotype, e.g. to diagnose increased metastatic potential, or to diagnose insulin resistance, or to diagnose disease, etc.

We discovered N-acetylneuraminic acid (NANA) is more highly expressed in breast cancer tumor initiating cells. From a diagnostic point of view, the presence of excess NANA can serve as a biomarker for tumorigenic potential. Once such differential expression is observed, detection methods such as antibodies or mass spectrometry can be utilized to monitor NANA expression (e.g., intracellularly or extracellularly) to help identify aggressive tumors. In summary, using the methods described herein for breast cancer cells, the specific breakdown of glucose was followed and NANA was discovered to be widely upregulated in more malignant cells. Enzymes were identified in NANA biosynthesis as new therapeutic targets, and the expression levels of the molecule was found to correlate with increased migratory potential.

The novel methods can also be applied to patient biofluids (e.g., blood, urine, plasma, and tissue samples) to discover metabolic differences that can serve as novel biomarkers for a particular disease.

Methods of Determining Candidate Therapeutic Agents

In various embodiments, the methods for identifying substrate metabolites differentially expressed by at least two populations of cells can further include the step of identifying a biosynthetic pathway involved in the generation of the substrate metabolites and identifying proteins/enzymes of the pathway that can be targeted to modulate the differential expression of the metabolite. In turn, these proteins and enzymes can serve as candidate targets for modulating the phenotype of the cells, e.g., a disease phenotype, metastatic potential, or resistance. Thus, the new methods provide a means for identifying therapeutic targets. Once the metabolite is identified and an NMR metabolite array has been created for a given sample, databases of biosynthetic pathways can be screened to identify the pathway of synthesis of the metabolite.

For example, the NMR metabolite array can be electronically linked to the Human Metabolome Database and/or ChemPub, to select possible therapeutic targets within the metabolite biosynthetic pathways and propose substrate-based inhibitors using the metabolite itself as a lead scaffold for drug design. A series of differentially expressed metabolites that can serve as biomarkers have been identified and described herein. Novel therapeutic targets within the biosynthetic pathways as well as FDA-approved drugs that show efficacy in the laboratory that could be rapidly translated into new applications in the clinic have also been identified.

The cell populations used in the various methods described herein can be from healthy or diseased subjects. The cells can be from isogenic populations. In some embodiments, the first population of cells and the second population of cells have different phenotypes (e.g., differ in metastatic potential, differ in response to insulin, or differ in expression of disease genes). Differential metabolites expressed in any phenotype can be assessed as compared to an isogenic cell that does not exhibit the phenotype. Phenotypes are easily identified by those skilled in the art, and include but are not limited to phenotypes associated with a particular disease or disorder.

In some embodiments, the first population of cells is a control population of cells and the second population of cells has been contacted with a test compound or agent (e.g., after treatment with the compound or agent). The disappearance of differentially expressed metabolites that are associated with a particular phenotype serves as an indicator that the test compound or agent is capable of inhibiting the phenotype, for example, inhibiting metastasis, or inhibiting the effects of the expression of a diseased gene. Alternatively, the appearance of a differentially expressed metabolite (e.g., one expressed only in normal cells as opposed to diseased cells) serves as an indicator that the compound or agent is useful for treatment of the disease. Thus, in various embodiments, the methods for identifying differentially expressed metabolites can be used to screen for compounds or agents that modulate a phenotype, which can be used for treatment of disease.

The metabolic consequences of overexpressing or inhibiting a gene of interest can be identified using the new methods described herein. In one embodiment, the method further comprises inhibiting or overexpressing a gene in one of the cell populations (e.g., the second population of cells). Similarly, the metabolic consequences of particular compounds or agents, e.g., to assess toxicity, also can be identified.

The test compounds or agents can be, for example, a small molecule, a nucleic acid RNA (e.g., siRNA or microRNA), a nucleic acid DNA, a protein, a peptide, or an antibody. The inhibitors can be selected from the group consisting of: a small molecule, a nucleic acid RNA (e.g., siRNA), a nucleic acid DNA, a protein, a peptide, and an antibody. In one embodiment, the inhibitor is an inhibitor of an enzyme (e.g., a neuraminidase inhibitor).

Methods of Treating Disorders with Therapeutic Agents

As described in the examples below, through the methods described herein, CMAS, NANS (also known as sialic acid synthase), and NANA cell-surface expression have been determined to be therapeutic targets that decrease migration of cancer cells and prevent tumor initiation in vivo. Thus, in another aspect, the present disclosure includes new methods for treating disorders such as cancer (e.g., by inhibiting metastasis and/or blocking tumor initiation) in a subject by administering an effective amount of an inhibitor of the targets discovered using the new methods described herein. In particular, the methods include administering to a subject in need thereof a therapeutically effective amount of an inhibitor of CMAS or NANS, or a therapeutically effective amount of an inhibitor or agent that lowers NANA expression. For example we have identified candidate CMAS inhibitors including a molecule we designed and synthesized, termed F-NANA, and already FDA approved influenza drugs, including Relenza and Tamiflu. The efficacy of these drugs in in vivo mouse models is being tested and because Relenza and Tamiflu have already been evaluated for safety in human subjects accelerated FDA approval for an investigational new drug is possible.

Application of the New Methods to Personalized Medicine

As mentioned, the new methods described herein have been successfully shown to characterize the metabolic differences in several oncology models using both cell lines and primary tissue. The methods have the potential to profoundly affect the strategies for designing novel therapeutic intervention and could be lay the foundation for a metabolite-based approach for "personalized medicine."

According to the National Institutes of Health, "personalized medicine" is a practice of medicine that uses an individual's genetic profile to guide customized decisions made with regard to the prevention, diagnosis and treatment of disease in that individual. To date, most efforts rely on genomic information to identify DNA mutations, amplifications, or deletions. Rarely, however, is a disease the result of a single genetic lesion, and it is often not obvious how genetic variations will manifest themselves. However, non-genetic changes, including epigenetic differences, can also have profound effects on gene expression and cellular properties. Further, many commonly mutated genes, such as in cancer, do not have small molecule inhibitors and are often termed "undruggable targets." Establishing the metabolic profile of key cells in an individual suffering from a disease, with the methodology described herein, could provide powerful information useful in diagnosing, treating and monitoring the disease state of an individual.

As noted, diseases are incredibly complex and heterogeneous, and the effect of a misregulated gene or genes is not always obvious; making it difficult to design the best therapeutic strategies for intervention. Metabolism on the other hand is the end product of the genome. Using the new platforms described herein, the metabolic differences in a specific patient can quickly highlight functioning or non-functioning pathways in that individual. Further, metabolic pathways have been extensively studied and in many cases inhibitors for metabolic enzymes, such antimetabolites, substances bearing a close structural resemblance to the natural metabolite, already exist and are already used in the clinic. Examples of such potential therapeutic discoveries based on the differential expression NMR analysis are also presented in detail below in the Examples. The aforementioned differential expression, for example of metabolites, can be a powerful tool for diagnosing, monitoring, and treating disease in a patient on an individual, customized basis. Examples of analysis using this protocol to deduce novel metabolism pathways and differential metabolite expression between wildtype and disease tissue are described herein.

EXAMPLES

The invention is further described in the following examples, which do not limit the scope of the invention described in the following examples, which do not limit the scope of the invention described in the claims.

The following examples discuss the novel protocols and the subsequent novel analysis methods that are used to efficiently determine the differential expression of metabolites in normal and disease state tissue. The results of such differential expression are described herein and are shown to be utilized in the design and identification of potential small molecule therapeutics.

Example 1

Methodology for the Screening Platform Utilizing NMR

Preparation of Biological Sample:

FIG. 1 provides an overall description of the platform. Approximately 20 million cells were used for each sample (however it is possible to use as few as 2 million). Before harvesting, $^{13}$C-labeled precursors (glucose and glutamine in these examples) were added directly to the media and allowed to incubate for a user-defined amount of a time and in this case 4 hrs. After aspirating the media and washing two times with phosphate-buffered saline (PBS), the cells were again counted and collected. An equal number of cells with no label were also harvested to serve as a $^{13}$C background control. Cells were lysed by the addition of ice-cold methanol, and an aqueous extraction was performed by adding equal parts water and chloroform. After centrifugation the water soluble and organic metabolites were separately collected, dried, and stored until ready to be further analyzed. No additional purification was performed.

Acquisition of Data with NMR:

2D NMR spectroscopy was employed primarily relying on heteronuclear single quantum correlation (HSQC) to identify metabolites. HSQC experiments provide one-bond correlation between a heteronucleus ($^{13}$C in the following examples, although other isotopes are feasible) and a proton. Crosspeaks arise due to transfer through the relatively large one-bond heteronuclear coupling, making it possible to identify shifts of directly attached nuclei. The unique chemical environment of each carbon atom paired to a proton gives rise to characteristic chemical shifts specific to a given metabolite. Reference HSQC spectra of purified metabolites (commonly available) were used for comparison. For example, at present the Human Metabolome Database (HMDB) contains information on 40,260 metabolite entries many with HSQC data.

To overcome the traditional drawbacks of 2D NMR metabolite profiling (large sample requirements and long acquisition times), several additional techniques were used to improve the resolution and reduce the time required for the analysis. As described above, in a first step, to decrease the amount of material needed cells were supplemented with $^{13}$C-labeled precursors (glucose, glutamine, pyruvate and amino acids were used but other substrates and other isotopes are also possible). Theoretically, this should decrease the cell number required by a factor of ~100. Partly due to varying ionic strengths, this does not always scale perfectly linearly and if there are no constraints regarding the sample size (i.e., using cell lines), it is recommended here that about 2-20 million cells be used for each analysis.

Example 2

Rapid Ultra High Resolution NMR Data Acquisition

Folding the Spectra:

While the aforementioned sample preparation alleviated the physical demands on the amount sample, the long acquisition time required to record high resolution 2D NMR spectroscopy was still a concern. To combat this, a multi-prong approach was taken: "folding" the spectra width, using random phase sampling (RPS), implementing non-uniform sampling (NUS) techniques and data extension in the analysis.

Figure 2A:
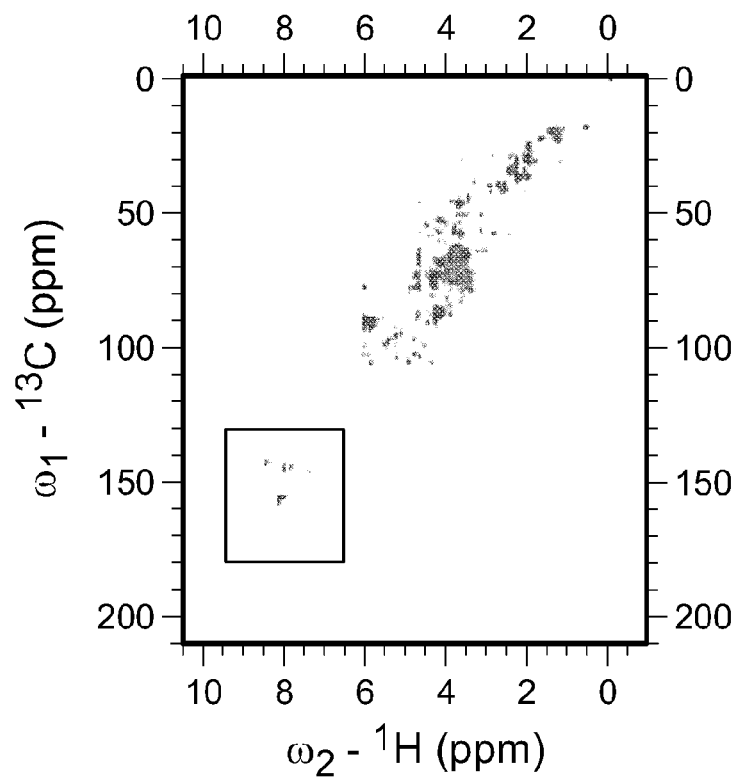
FIGS. 2A-F detail each step of the acquisition and processing in the NMR methods that allow for rapid, unbiased, ultra-high resolution metabolite profiling.
Figure 2B:
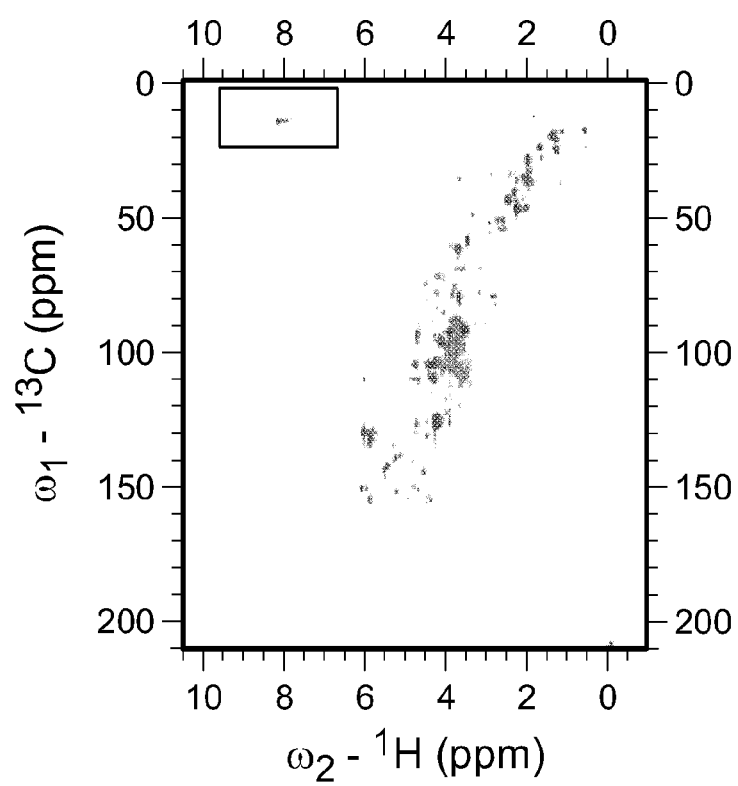
Figure 2C:
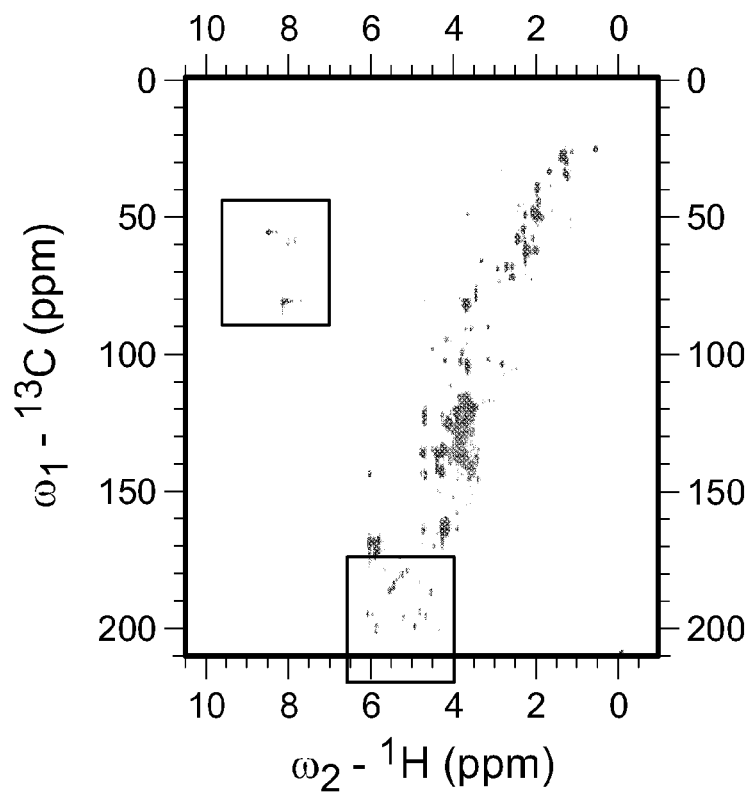
Figure 2D:
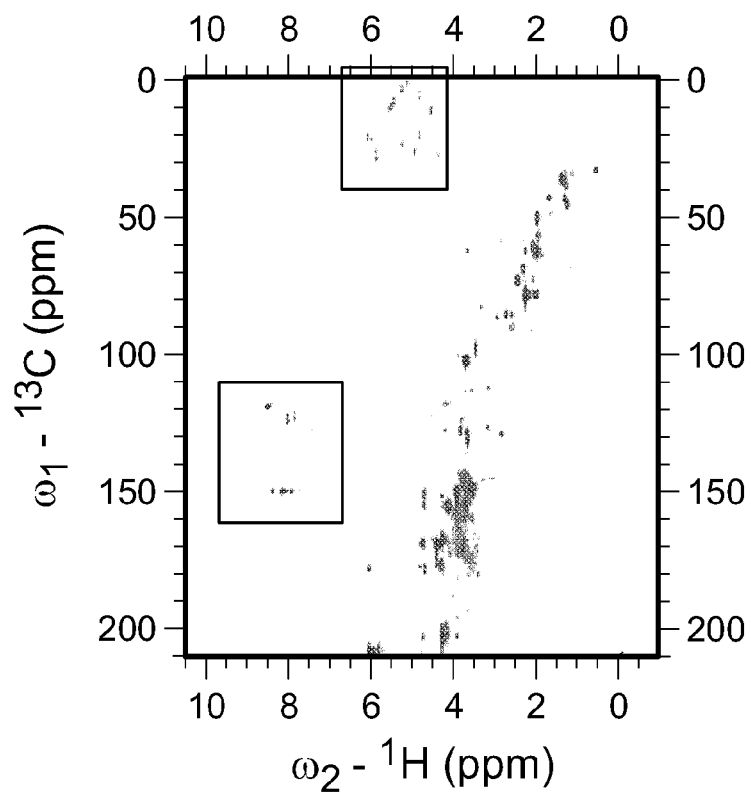

As described above, the spectral width (sw) is the range of frequencies over which NMR signals are to be detected. Metabolite mixtures contain diverse molecules, and the spectral width necessary to cover all potential carbon chemical shifts spans over ~220 ppm. In FIG. 2A, the HSQC spectra for all water soluble metabolites in KRAS mutant pancreatic cancer cells is shown. In this instance the 13C-sw spans 220 ppm and a total 1024 points were collected. By solving the equation, resolution=SW/TD (where TD is the total data points), we observed the resolution was limited to ~107 Hz/point. However, if you examine FIG. 2A closer, the majority of metabolites run along a diagonal and most the spectrum is empty. Collecting points along the entire sw greatly diminishes resolution, and as acquisition time is the reciprocal of resolution, experimental time is also wasted. As such we gradually decreased the sw to increase the resolution. FIG. 2B shows an HSQC of the same sample with 140 ppm sw and as a result resolution of ~68 Hz/point, FIG. 2C with sw of 110 ppm and as a result 54 Hz/point resolution and FIG. 2D with 90 ppm sw generates ultra-high resolution of ~44 Hz/point. In each of the folded spectra the aliased peaks are easily identifiable and the true chemical shifts can be can be back calculated using the following equation ($\delta obs = \delta + sw$). Of note, the maximum resolution due to C-C scalar coupling is ~35 Hz. Using our folding strategy we are able to obtain ultra-high resolution spectra.

Of note, to provide optimal flip angles uniformly across the large carbon spectral width, broad band adiabatic shaped pulses were utilized for all 180 degree pulses along the carbon channel. This is especially important for enabling efficient coherence transfer among scalar coupled spins.

Non Uniform Sampling and Extension of Data:

The measured "free-induction decay" (FID) of an NMR sample is created by the oscillating current generated by the precession of all magnetized bonds. This signal decays due to nuclei in other molecules creating spin-spin decoherence. The rate at which this occurs is known as the transverse relaxation rate (T2). For any NMR experiment it is widely viewed that to obtain maximum resolution one should collect points in the indirect dimension close to 1.2*T2. However, metabolites move rapidly with molecular motion correlation times on the average of $10^{-12}$ to $10^{-11}$ sec. Due to this rapid movement, for many metabolites there is little spin-spin decoherence and the T2 rates are almost infinitely long. Thus collecting ultra-high resolution metabolite data is theoretically possible but in practice it would require extremely long measurement times and in most experiments only a subset of data is collecting sacrificing resolution for speed.

Figure 2E:
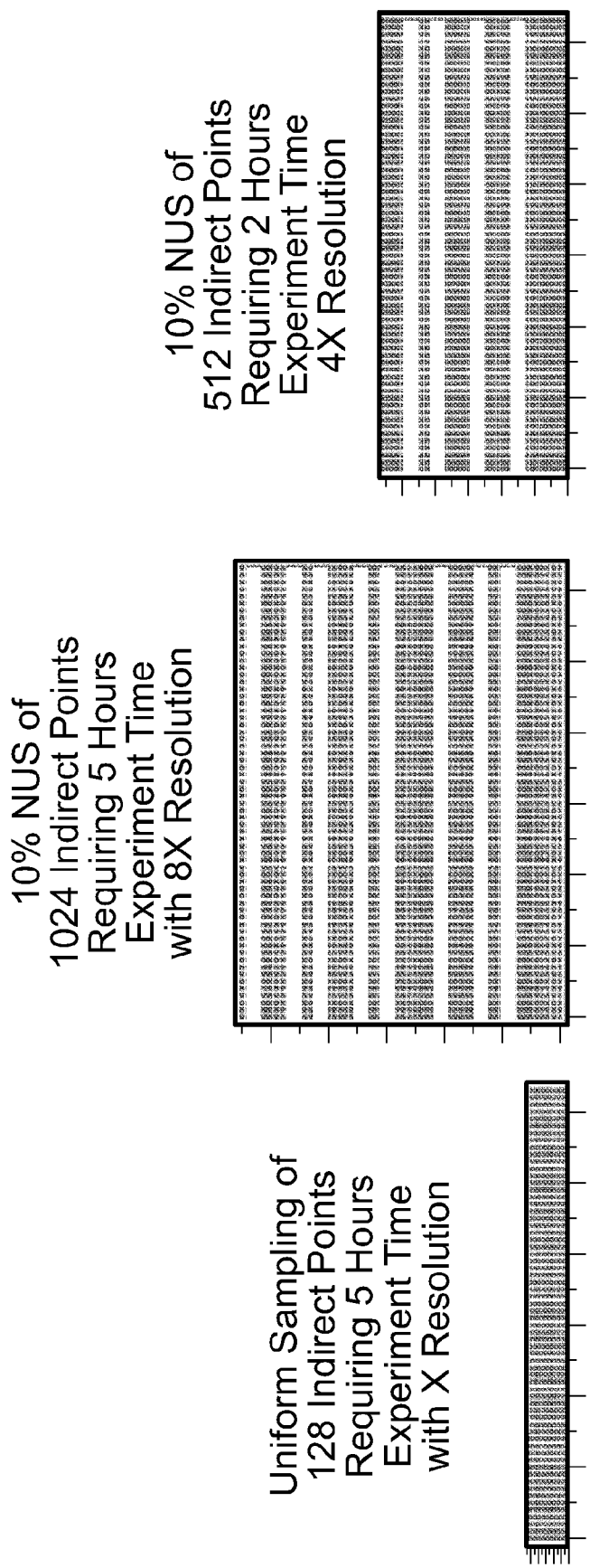

By employing non-uniform sampling (NUS) techniques that are outlined in FIG. 2E we were able to not only greatly increase the resolution of our data but also increase the speed at which we recorded high resolution spectra. For example using the same sample we could perform a uniformly sampled experiment with 128 indirect points in 5 hours with X resolution, using NUS we could collect 10% of 1024 points and in equivalent time to generate a spectra with 8× resolution, alternatively we could sample 10% of 512 points increasing the resolution by 4× and decreasing the acquisition time by ~40%.

Figure 2F:
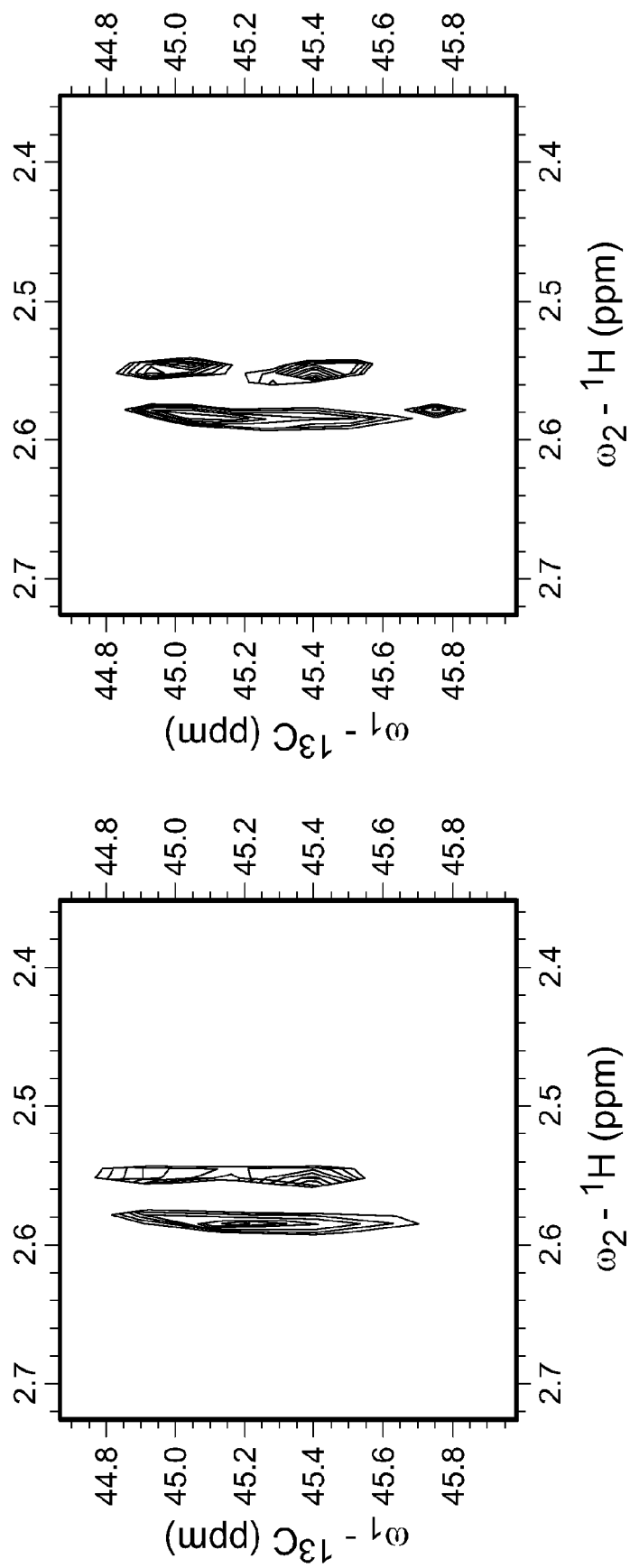

The Poisson-gap distribution was selected for the sampling schedule followed by forward maximum (FM) entropy reconstruction. Metabolite mixtures contain molecules at various concentrations, and this has been shown to be the most effective method in detecting weak peaks. In addition, to further enhance our resolution we created a "data-extension" add-on, in which before reconstruction the total number of points in the indirect dimension is artificially doubled. The first half of the NUS data set is reconstructed using the sparsely sampled data and filling in the missing points according to FM reconstruction. The second half of the data is completely built using iterative soft thresholding. As shown in FIG. 2F this increased our resolution by 2-fold without affecting acquisition time.

Analysis of Metabolites in the Water and the Organic Layer:

While it is not necessary to follow each step, this method allows for a full metabolic profile of both water soluble or organic metabolites. FIG. 3 shows the HSQC of water based metabolites (FIG. 3A) and organic based metabolites (FIG. 3B) from the same ~2 million p53 deficient lung cancer cells and each experiment required only 1 hour of acquisition time. Equivalent spectra using 13C-natural abundance and standard NMR techniques for the same sample amount would require several days. Both spectra are extremely well resolved, making it easy to identify metabolite resonance peaks. Importantly many M/S methods have struggled to accurately detect lipids, using our method, as shown in FIG. 3B, the resonances from organic molecules are readily identifiable.

Example 3

Analyzing Metabolite NMR Data

NMR Analysis:

As summarized in FIG. 4, a custom "NMR Metabolite Array" program was created to automate the NMR analysis process using the method herein described. First, the spectra are phased, aligned, and scaled with an internal control. 1 mM 4,4-dimethyl-4-silapentane-1-sulfonic acid (DSS) was added into each sample, and its concentration was used as a reference to allow relative quantification comparisons between samples to be made. We created an automatic peak picking program to generate peak lists for each sample, where each resonance peak was converted into an X, Y coordinate with an intensity value. Next we created a "MASTER PEAK LIST" program that generates a "master" look up table for all the resonances in the spectra under investigation and was subsequently run.

In short, this program reads all X, Y points from the individual peak list files, removes duplicates within defined tolerances and writes the resulting set of peaks to a standard output. Depending on the analysis it is possible to input the entire HSQC data from the Human Metabolite Database into the master peak-list. Taking this approach requires longer computation times, and in most cases is unnecessary. Creating master look up tables for the spectra that are specifically being investigated is preferred.

Next, NMR arrays are generated for each sample in which the individual peak list and master peak list were combined to fill in the intensity for resonances for all possible metabolites. If a metabolite is expressed in a test sample, the program will select that intensity value. If it is not present, the intensity is set at zero or an arbitrary number. The NMR arrays can now be analyzed via traditional statistical analysis programs to identify the differentially expressed resonances between spectra. The resonance frequencies can then be uploaded directly into the Human Metabolome Database to identify which metabolites are differentially expressed. Candidate metabolites can then be confirmed via additional NMR or M/S experiments.

Example 4

Analysis of Differentially Expressed Metabolites

A Novel Approach

Figure 5:
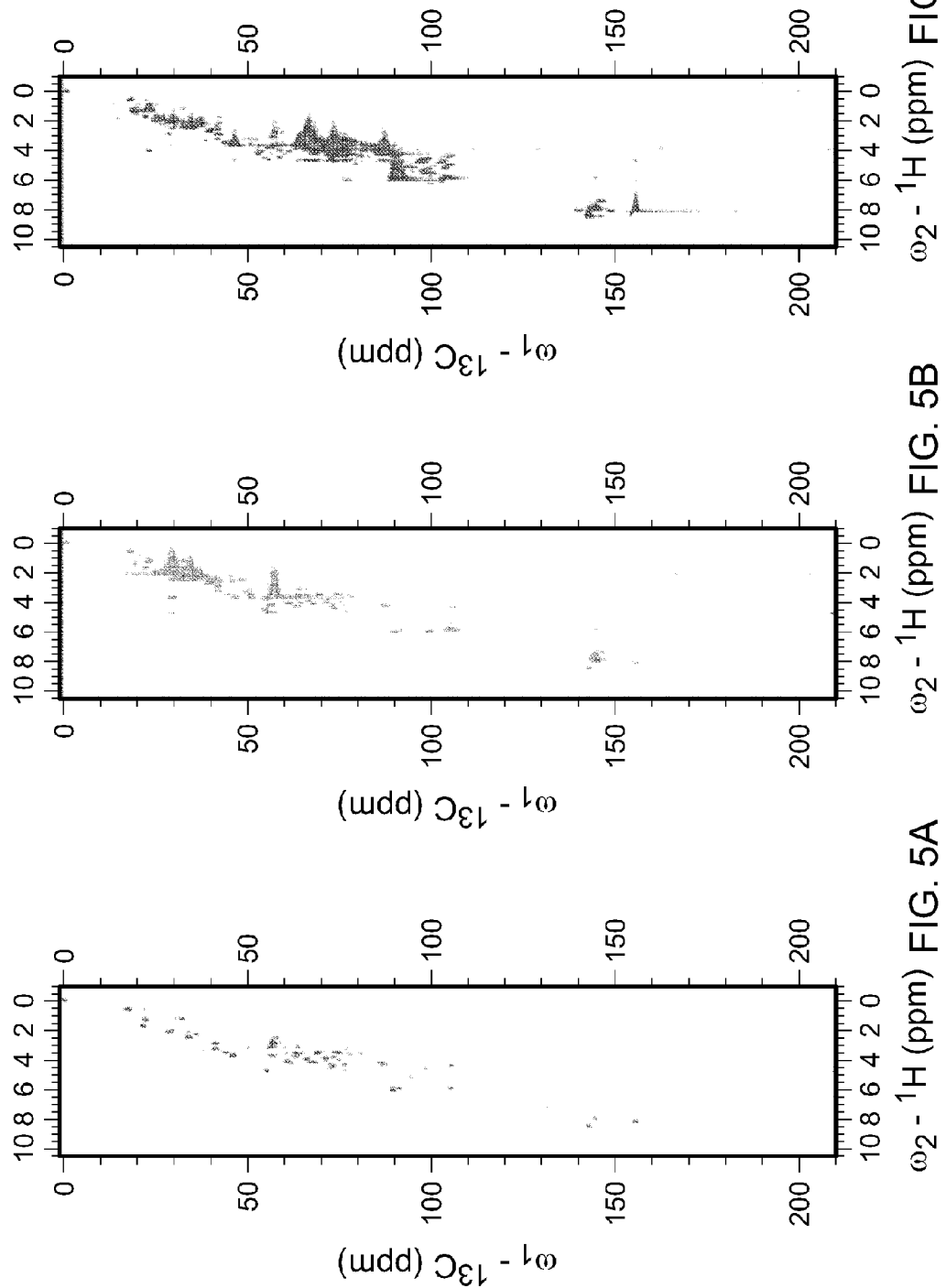
FIGS. 5A-C are a set of $^{13}C$-$^{1}H$ HSQC resonance spectra of water-soluble metabolites from 20 million unlabeled (5A)$^{13}C$-glutamine incubated (5B) and $^{13}C$-glucose incubated (5C) breast tumor initiating cells.
Figure 6:
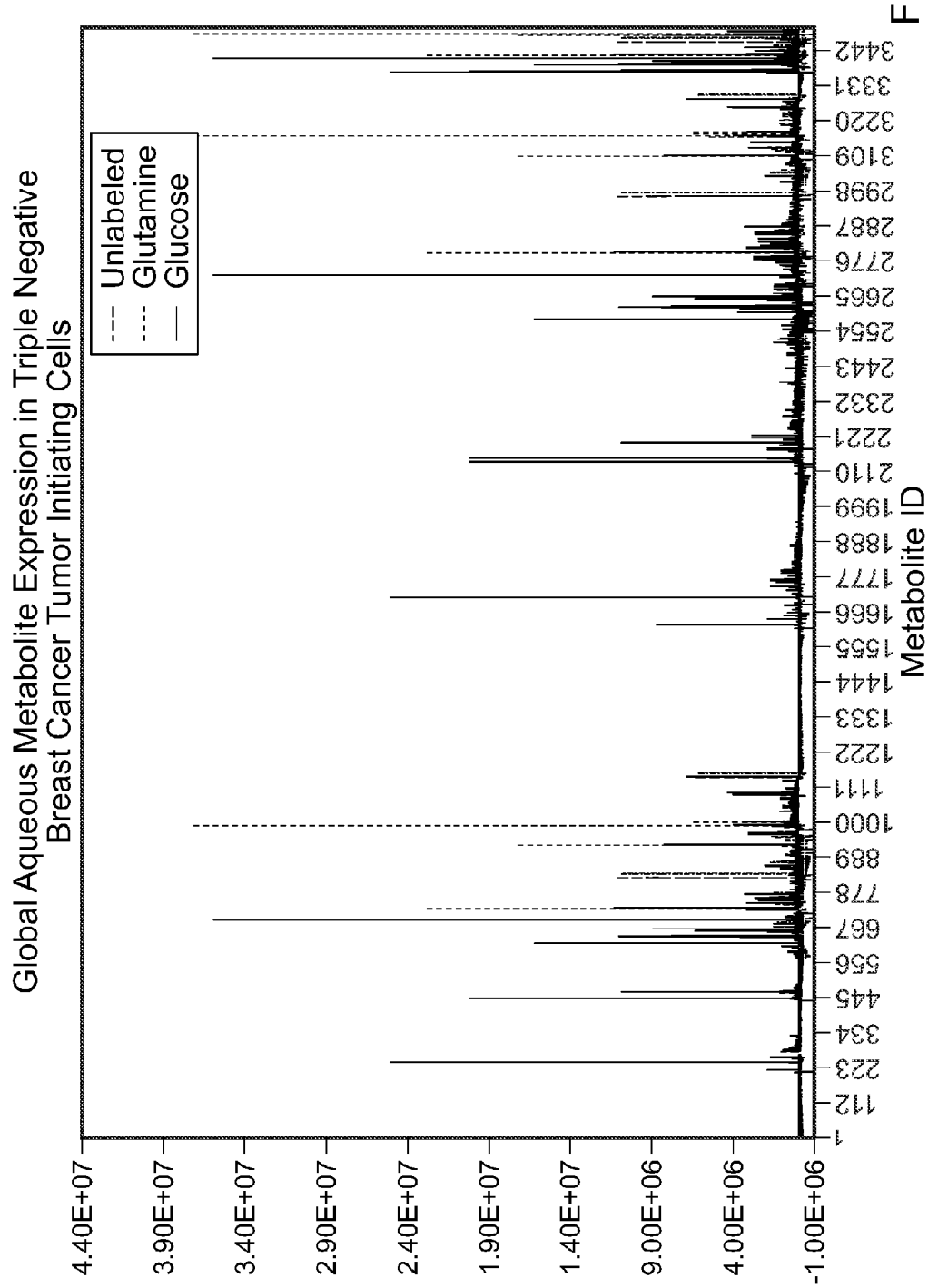
FIG. 6 highlights the information available in the NMR arrays described herein. Using the unlabeled, glutamine, and glucose spectra in FIGS. 5A-C, a master look up was created to generate metabolite IDs for all possible resonance metabolites that and these are listed on the X-axis. The Y-axis displays the relative intensity of each resonance in each condition, highlighting the differential glucose and glutamine derived metabolites.

Background Correction:

To monitor the flux of a given precursor, a separate spectra with an equal number of cells with no labeled precursor was recorded. The spectra from the unlabeled cells represent the $^{13}C$ background within the cell and can be subtracted from the test spectra to specifically follow the metabolic breakdown of the $^{13}C$ labeled substrate. Glucose and glutamine are two of the main energy sources within a cell, and the metabolic breakdown of each precursor is well characterized. To examine the flux of glucose and glutamine into specific pathways, $^{13}C$-$^{1}H$ HSQC spectra of equal number of breast tumor initiating cells with no labeled precursor and either $^{13}C$-glutamine or $^{13}C$-glucose added as substrate were recorded. As shown in FIG. 5A with this limited number of cells, very few signals arise from the $^{13}C$ background, and the glutamine (5B) and glucose (5C) spectra are quite distinct. By creating NMR arrays we were able to convert the complex NMR data into standard text files. The intensity values for resonances in the unlabeled sample were subtracting from the matching signals in the glutamine or glucose arrays. As shown in FIG. 6, by plotting the intensity value and resonance metabolite ID from the NMR array it is possible to identify changes specific to glucose or glutamine flux through a given sample. The X-axis lists all the resonance metabolite ids for every metabolite identified from the HSQC spectra of FIG. 6b and FIG. 6c. The Y-axis highlights how the intensity of each resonance changes in each condition. As expected, it is clear glutamine and glucose cause flux into different metabolic pathways. The resonance metabolite IDs correspond to specific $^{13}C$-$^{1}H$ chemical shifts which can uploaded into the Human Metabolome Database to identify the differential metabolites.

Example 5

Identifying Differentially Expressed Metabolites in Triple Negative Breast Cancer Tumor Initiating Cells Protocol:

Originating from the same normal breast tissue, BPLER and HMLER cells were transformed with identical genetic factors but were propagated in different culture media. BPLER are highly tumorigenic and have an increased metastatic potential over that of HMLER cells. Less than 50 BPLER cells injected into the mammary fat pad of a mouse result in the development of a tumor, while more than $10^{-6}$ HMLER cells are required to form a tumor in vivo (Table 2, below). BPLER cells are a model cell line for triple negative breast cancer tumor initiating cells, and BPLER tumors histologically resemble that of triple negative breast cancer patients. According to the protocol about 20 million BPLER and HMLER cells were cultured in the presence of uniformly labeled $^{13}C$-glucose, and subsequently harvested and lysed. The aqueous layer was then collected, dried, and re-dissolved in ultra-pure D2O and ready for NMR analysis. The organic layer was stored for future examination.

TABLE 2

| | Tumors Formed | | |
|---|---|---|---|
| Cells | BPLER | HMLER | MCF7 |
| 5 × 10$^4$ | 4/4 | 0/4 | 0/4 |
| 5 × 10$^3$ | 4/4 | 0/4 | 0/4 |
| 5 × 10$^2$ | 4/4 | 0/4 | 0/4 |
| 5 × 10 | 4/4 | 0/4 | 0/4 |

Using the new platform methodology described herein, the rapid, unbiased, ultra-high resolution NMR metabolite screening was performed. Examples of resulting $^{13}C$-$^{1}H$ HSQC for BPLER and HMLER cells are shown in FIGS. 7A and 7B respectively.

Results:

Using our custom NMR analysis program, the resonances in each spectra were converted into NMR arrays. FIG. 7C summarizes the information. By combining all replicates from both cell lines approximately ~2100 resonances were identified. The metabolite ID of each resonance is listed on the X-axis. The relative intensity of each resonance is plotted on the y-axis. From this analysis we observed a high degree of similarity between the metabolite resonances of each cell line (>75% of the resonances were present in both cell lines). However several resonance peaks that were common to both cell lines had varied expression, while some peaks were unique to HMLER cells and others specific to BPLER. To confirm the arrays accurately reflected the HSQC data, as shown in FIG. 7D the region of the HSQC spectra that was predicted to have resonances specific to BPLER cells in the NMR array was expanded and indeed resonances were only found in the BPLER spectra.

Using the NMR arrays we were able to quickly identify resonances that were specifically enriched in BPLER tumor initiating cells. Table 3 highlights the top resonances most enriched in BPLER tumor initiating cells. Shown are the metabolite IDs from the array, as well as the corresponding $^{13}C$-$^{1}H$ data.

TABLE 3

| Metabolite Resonance ID | 13C | 1H |
|---|---|---|
| 589 | 62.993 | 3.842 |
| 1951 | 65.98 | 3.823 |
| 283 | 68.633 | 4.248 |
| 1381 | 69.973 | 4.002 |
| 402 | 42.028 | 2.193 |
| 1602 | 72.951 | 3.739 |
| 245 | 72.849 | 3.953 |
| 1333 | 42.015 | 1.814 |
| 119 | 106.501 | 6.151 |

These resonances were input into the Human Metabolome Database and 6 of the 9 resonances, highlighted in yellow were predicted to be from N-acetylneuraminic acid (NANA), strongly suggesting NANA is the metabolite corresponding to the differentially expressed resonances identified in the NMR arrays.

Figure 8C:
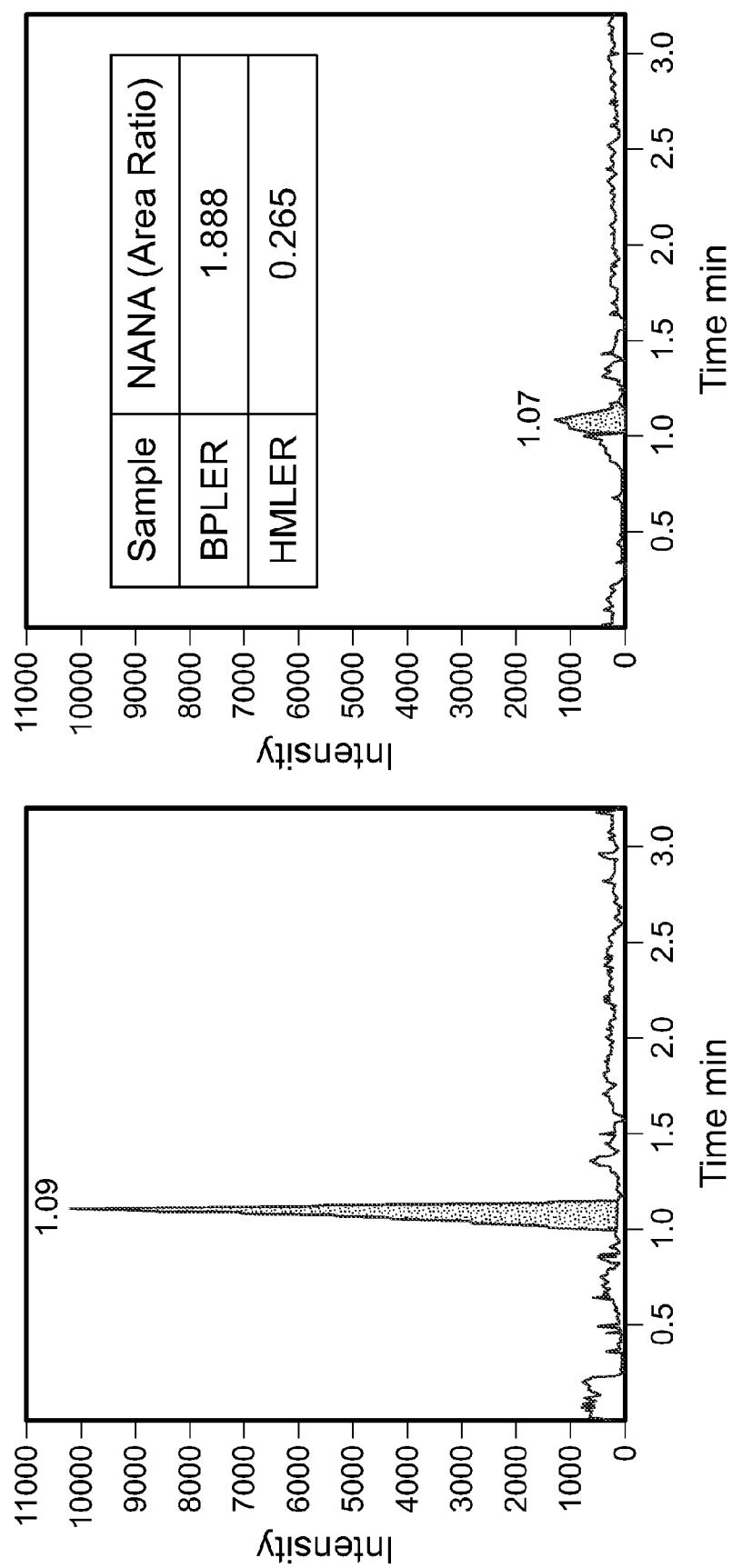

Several additional steps were taken to confirm NANA is indeed upregulated in BPLER tumor initiating cells. First, $^{13}$C-$^{1}$H HSQC of pure NANA shown in FIG. 8A contains cross peaks at approximately the same location as those found over-represented in the BPLER spectra. Second, we designed custom NMR pulse programs to specifically examine NANA. In NANA biosynthesis the C2 of glucose and a nitrogen atom of glutamine are joined to form a carbon-nitrogen bond. As such BPLER cells were incubated with $^{13}$C-C2 glucose and $^{15}$N-glutamine, and a HCN experiment was recorded to detect metabolites resonances that contain a hydrogen, connected to a carbon, that is also connected to a nitrogen atom (HCN). In this experiment, as shown in FIG. 8B BPLER cells contain a differentially expressed resonance at the same position as would be expected in the NANA standard. Lastly, mass spectrometry experiments shown in FIG. 8C, confirmed NANA is approximately 7-fold higher in BPLER tumor initiating cells by performing multiple reaction monitoring LC/MS using electrospray in the negative mode. The reported values are the area under the curve for NANA expression in each cell line.

Using Results of Differentially Expressed Metabolites to Develop Diagnostics:

By following glucose flux within BPLER cells (i.e. subtracting background $^{13}$C and tracing specific breakdown of glucose), the tumor initiating cells were observed to divert part of their glucose metabolism to NANA production. NANA is 9-carbon sugar that is often incorporating onto the cell surface of glycoproteins. Previous reports identified that wheat-germ agglutinin (WGA) has a strong affinity for NANA-modified proteins. Using rhodamine labeled WGA, we preformed immune-fluorescent microscopy shown in FIG. 9 and observed BPLER cells have increased NANA expression on their cell surface. Thus, NANA itself represents a novel diagnostic to specifically identify breast tumor initiating cells, and WGA, and similar molecules that specifically recognize NANA and NANA modified molecules could provide new tools to detect & isolate tumor initiating cells or those with increased malignant potential.

Example 6

Identification of a Target Utilizing the Differential NMR Data

Figure 10:
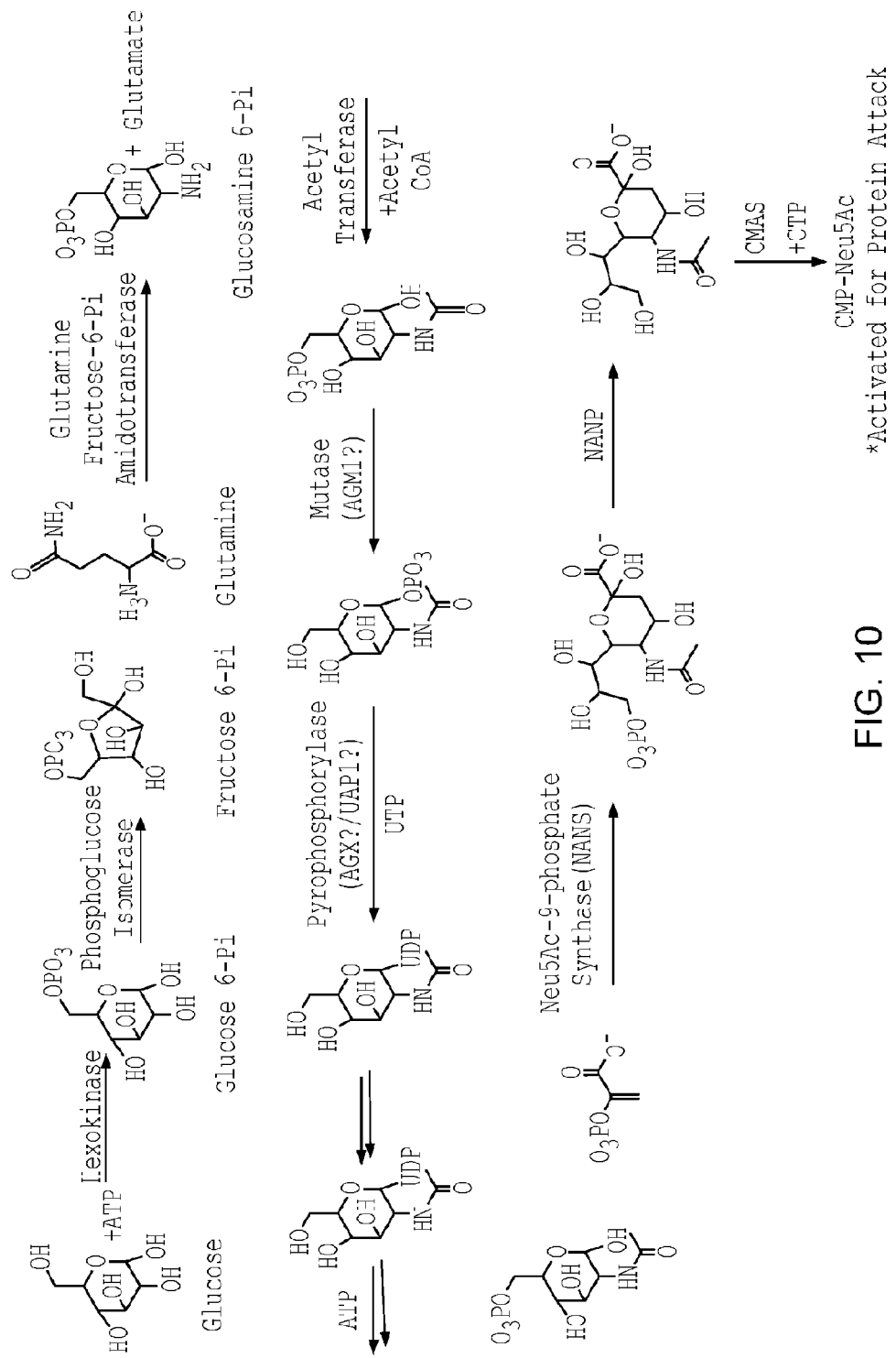
FIG. 10 is a schematic diagram depicting the enzymatic steps to convert glucose to NANA, in which N-acetylneuraminic acid synthase (NANS) and N-acylneuraminate cytidylyltransferase (CMAS) are key enzymes.
Figure 11:
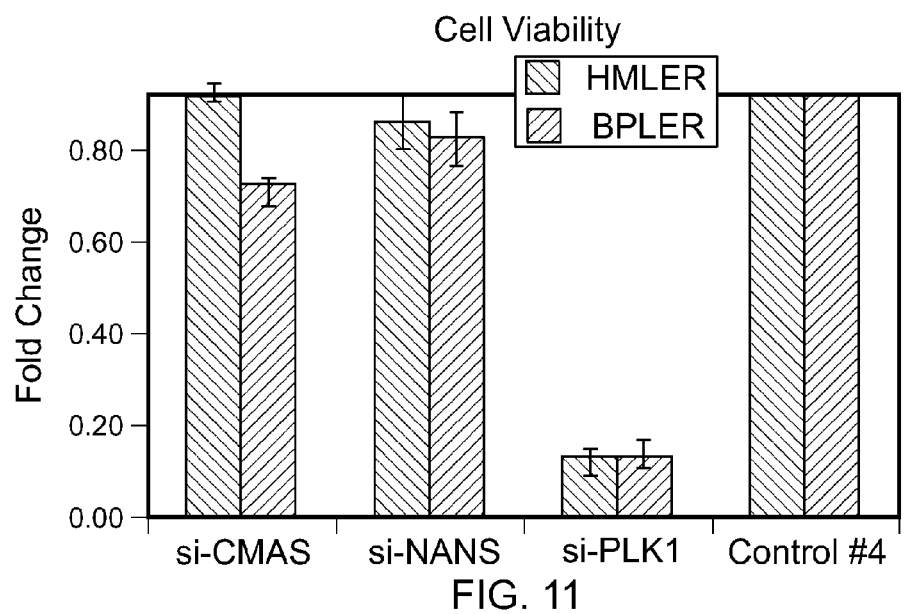
FIG. 11 is a bar graph showing the effects on proliferation by downregulating CMAS, NANS, and PLKI via siRNA on the viability of HMLER and BPLER cells.

NANA is a sugar that is often incorporated onto cell surface proteins. Shown in FIG. 10 NANA is derived from glucose by about 15 distinct enzymes including key enzymes NANS and CMAS. Using CelTiterGlo, a well-known assay for cell viability, it was observed that knockdown of NANS or CMAS had little to no effect on cell viability or proliferation of the cells (FIG. 11), whereas knockdown of PLK1 enzyme lead to total cell death.

However, NANA is incorporated on the cell surface of several proteins involved in cell adhesion, and loss of NANA was suspected to affect cell motility. Using a cell migration assay, cells were cultured in a dual-chamber containing small pores at the bottom of the top chamber, malignant cells (especially those with metastatic potential) are able to migrate through the pores and form colonies. As expected, shown in FIG. 12 BPLER have an increased migration rate as compared to HMLER cells due to their increased turmorigenic properties. However, the knockdown of NANS or CMAS completely abolished the cells' ability to migrate to the lower chamber, while cells transfected with control siRNAs maintained normal migration. To confirm NANA expression directly influences motility, a rescue experiment was performed in which cells transfected with siRNAs against NANS or CMAS were supplemented NANA. In the presence of NANA they were able to partially restore the migration phenotype. These results of several migration studies are quantified in FIG. 12B. These results suggest NANA expression is crucial for cell migration and could be important for metastasis. Monitoring NANA expression could predict the metastatic potential of a cell. In addition both NANS/CMAS are novel key targets to manipulate migration and metastasis.

Example 7

CMAS Increase Cell Migration

Figure 12A:
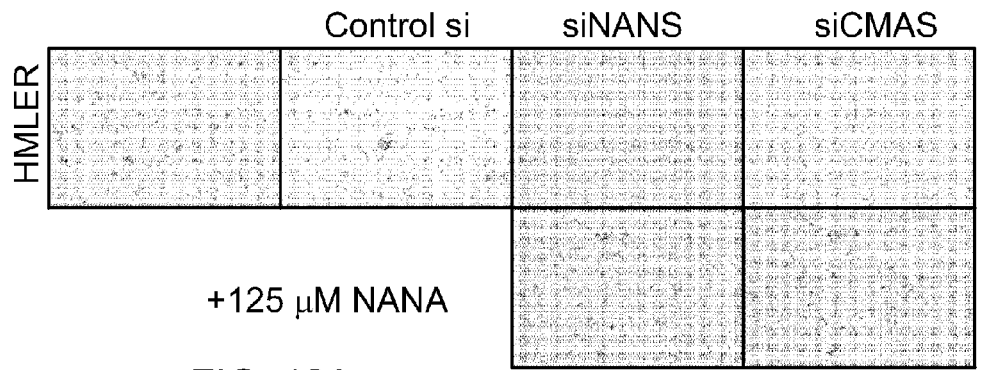
FIGS. 12A-C are a series of images that provide an overview of the NANA effect on cell migration of BPLER and HMLER cells.
Figure 12B:
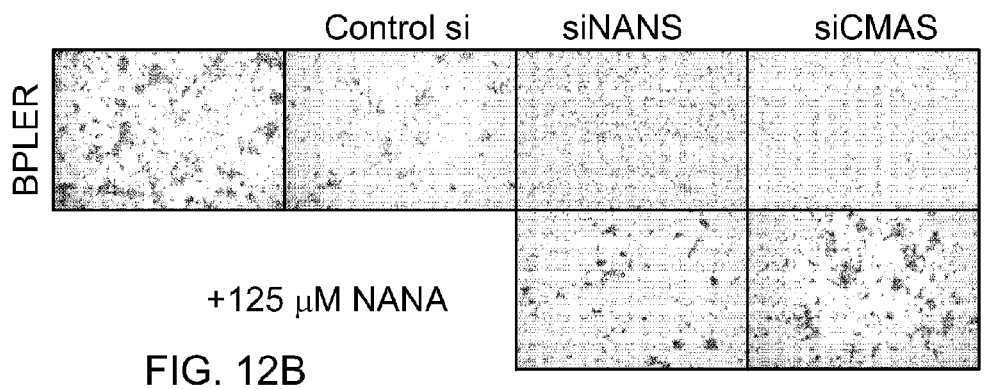
Figure 12C:
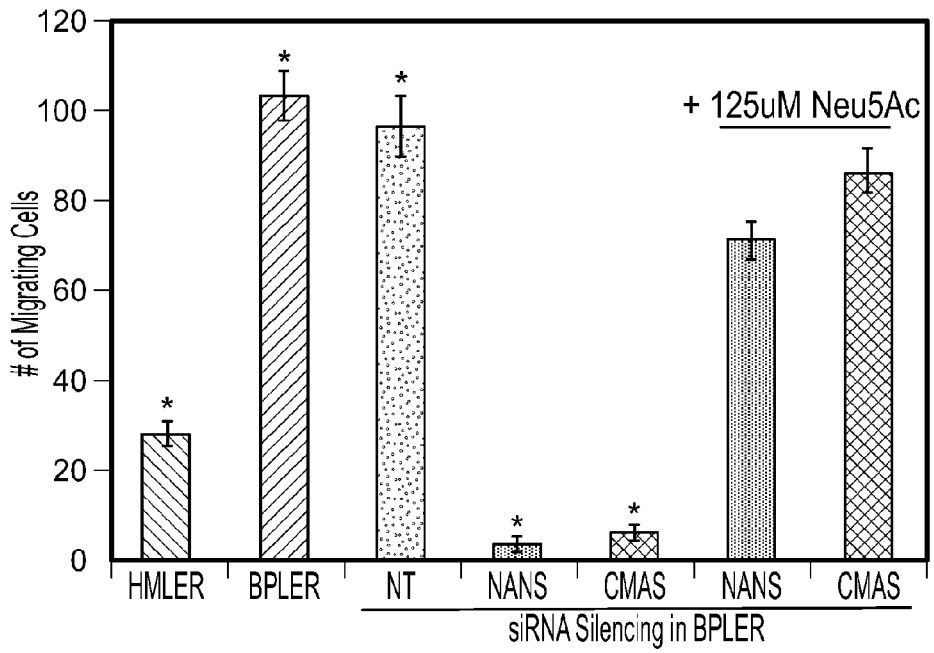
Figure 13A:
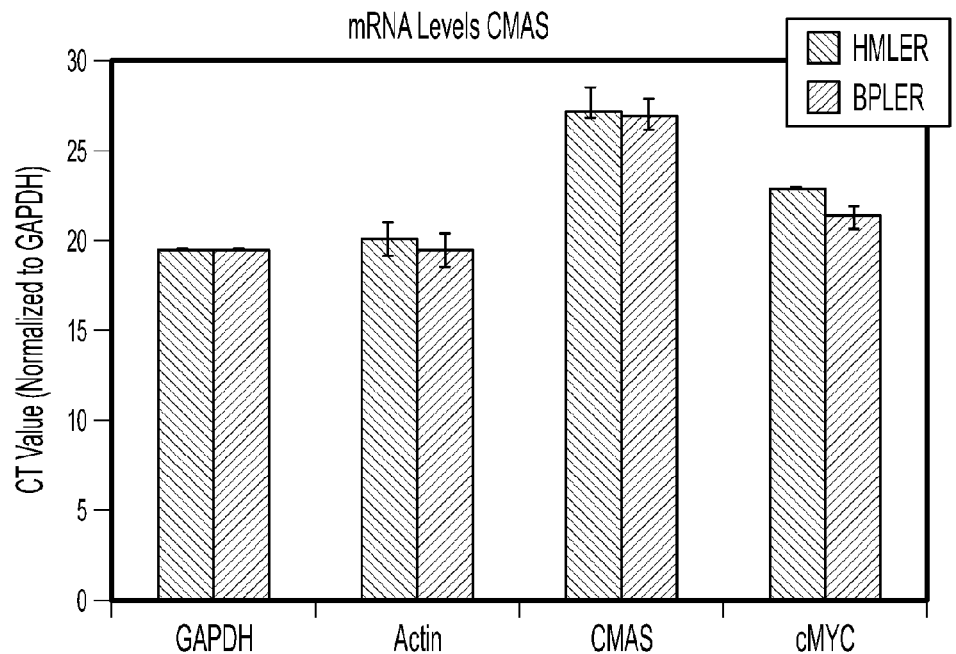
FIGS. 13A-B are a bar graph depicting the quantitative PCR (mRNA levels) of CMAS and cMYC (13A) and a Western Blot analysis of NANS and CMAS expression (13B), respectively, in HMLER and BPLER cells.
Figure 13B:
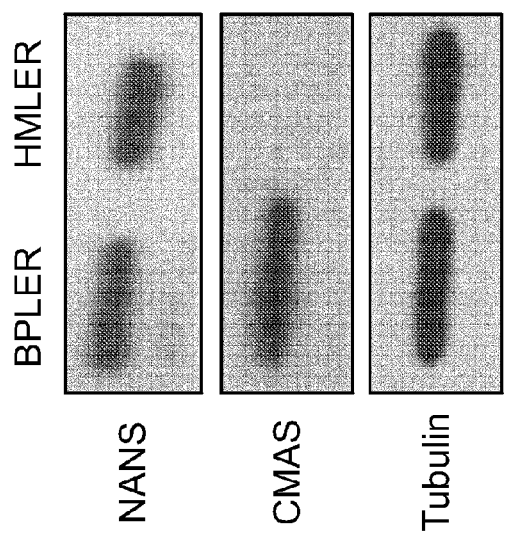
Figure 14A:
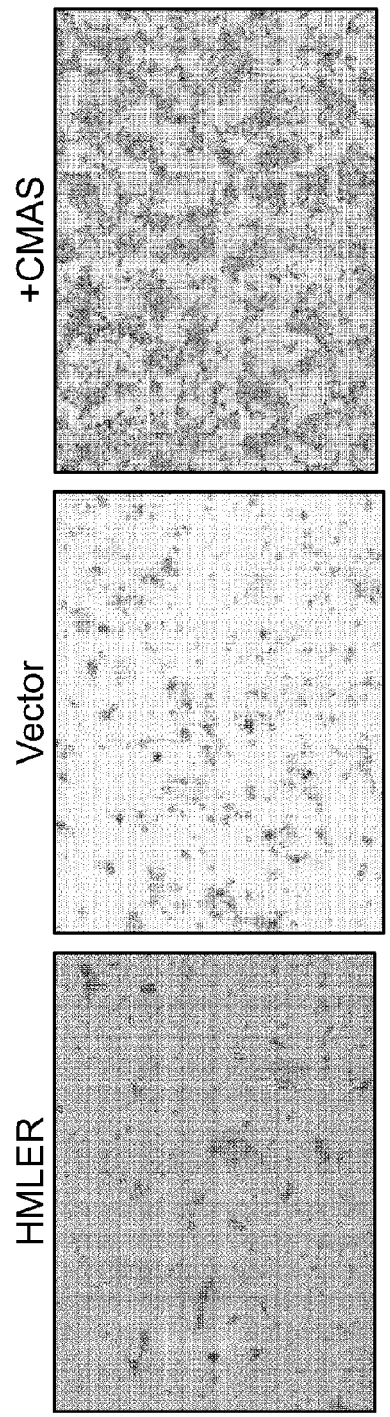
FIGS. 14A and 14B are immunohistochemistry images of the effect of CMAS expression on cell migration.
Figure 14B:
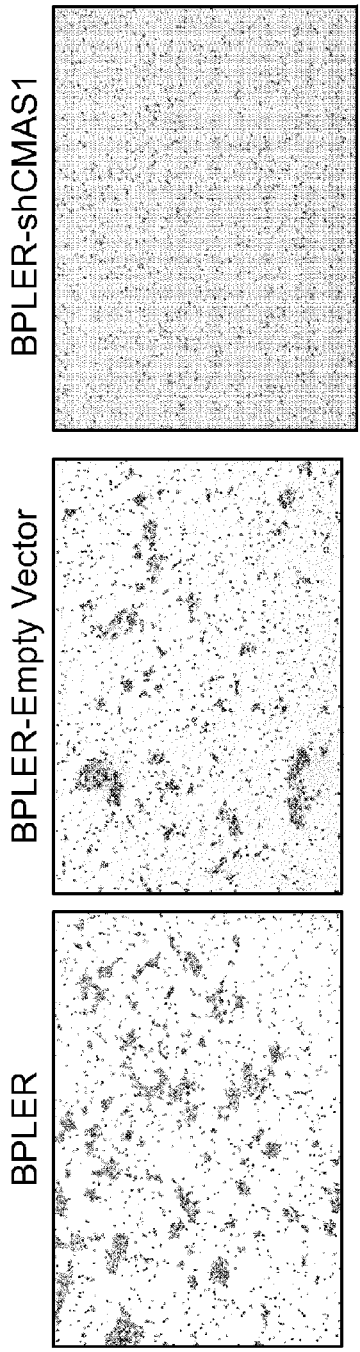

As mentioned, the knockdown of NANS and CMAS, key enzymes used to generate and attach NANA to proteins, had no effect on cell proliferation but greatly reduced the ability of BPLER cells to migrate (shown in FIG. 12). While the mRNA level of CMAS and NANS was equivalent in HMLER and BPLER cells, we observed the protein expression of CMAS is dramatically over expressed in BPLER tumor-initiating cells (FIG. 13). To determine if CMAS expression contributes to the malignant phenotype of tumor initiating BPLER cells, non-aggressive HMLER cells were transfected with a plasmid to force the expression of CMAS. Using the previously described cell migration assay, as shown in FIG. 14A HMLER cells with enhanced CMAS expression dramatically increased their migration potential by several fold compared to the control. The reciprocal experiment was also performed and stable CMAS knockdown BPLER cells (BPLER-shCMAS1) were created. As expected, shown in FIG. 14B these cells were not able to form colonies in the same migration assay. These results suggest CMAS protein expression is pivotal in cell migration and/or metastasis. To date there have been no references to the role of either NANS or CMAS in cancer. This could be in part due to most techniques relying on sequencing and/or microarray experiments that only examine mRNA levels. This highlights the strength of our method. By probing metabolites, NANA was identified as being expressed significantly higher in breast tumor-initiating BPLER cells. By subsequently probing the enzymes in its biosynthetic pathway, a novel, potent target that could be important for tumorigenicity was discovered.

Example 8

CMAS Impacts Tumor Formation Initiation

Figure 15A:
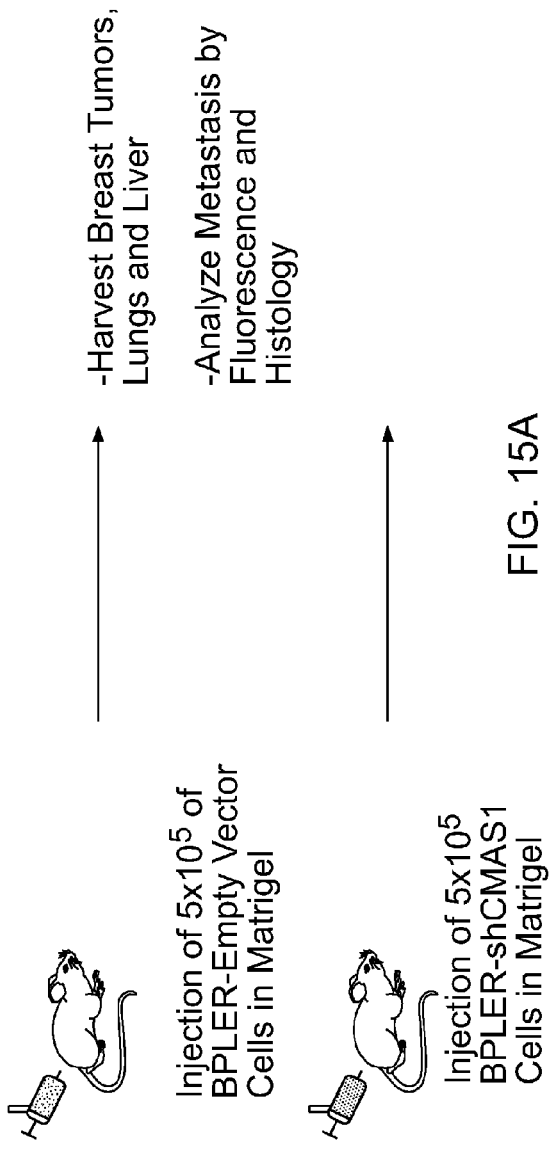

To determine how loss of CMAS/NANA expression effects the tumor initiation in vivo we performed the experiment outlined in FIG. 15A. As described above stable CMAS knockdown BPLER cells (BPLER-shCMAS1) were created that do not express CMAS protein. In our experiment 500,000 BPLER cells over expressing an empty vector (control) and 500,000 BPLER-shCMAS1 cells (which do not express CMAS) were injected into the mammary fat pad of NOD/SCID mice. The goal was to analyze differences in tumor size and the number of metastasis between each group. Every three days for 45 days the mice were examined for palpable tumors, and if detected the tumor height, length and width were directly measured to calculate tumor volume. As shown in FIG. 15B, within 45 days, 4/4 of the control mice had developed large primary tumors. Amazingly, none (0/5) of BPLER-shCMAS1 mice had any palpable tumors. Indeed after 90 days the mice injected with BPLER-shCMAS1 cells remained tumor free. Taken together the in vitro and in vivo data suggest that CMAS is a completely novel and bona fide therapeutic target for cancer.

Example 9

Figure 16A:
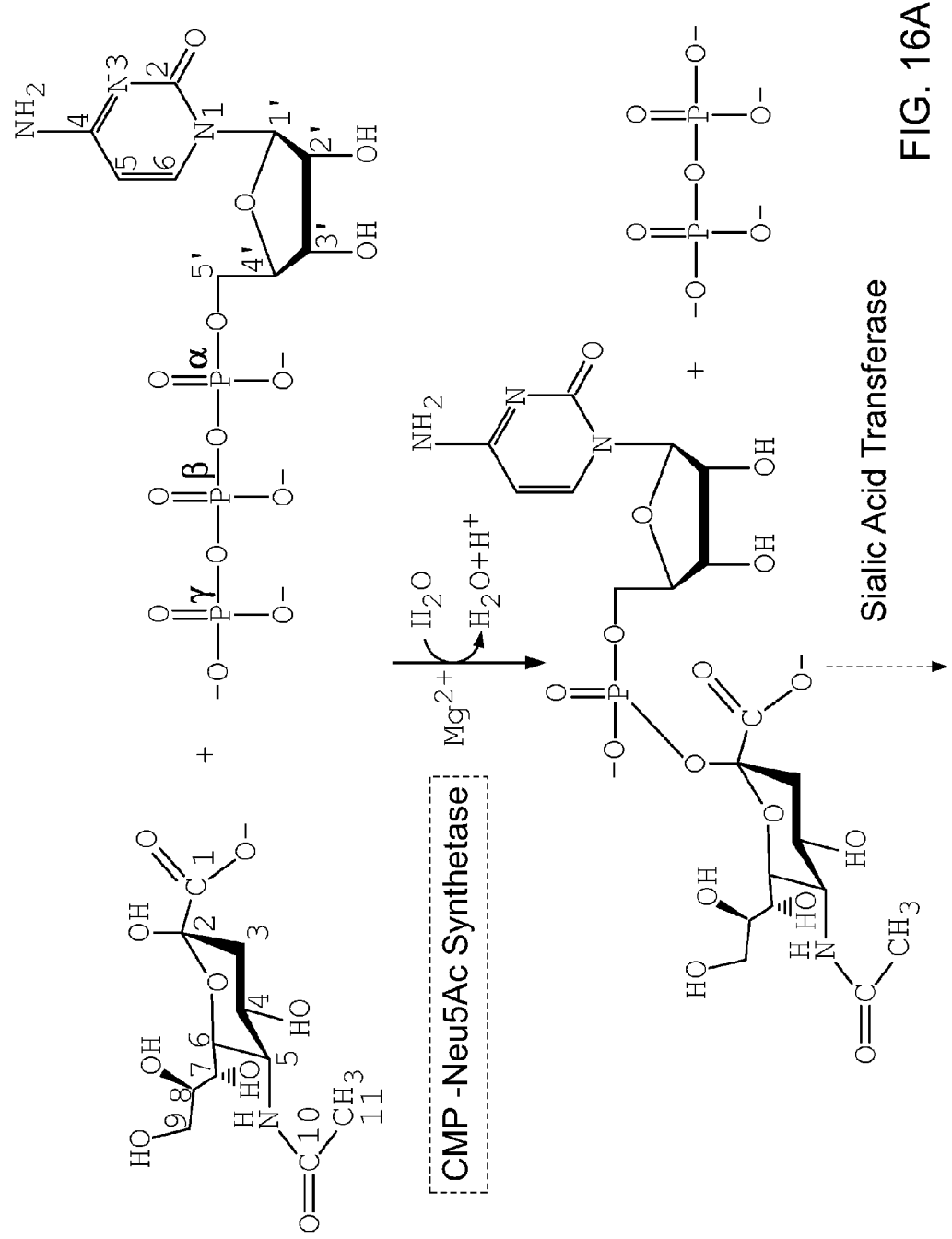
Figure 17A:
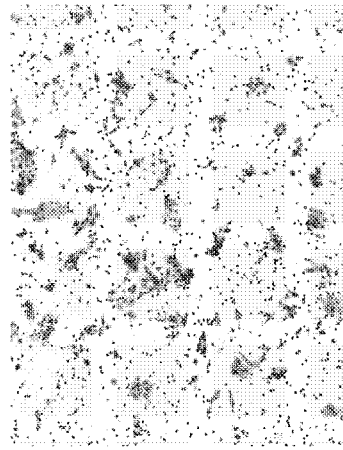
FIGS. 17A and 17C are the chemical structures of (2R,3R,4S)-4-guanidino-3-(prop-1-en-2-ylamino)-2-((1R,2R)-1,2,3-trihydroxypropyl)-3,4-dihydro-2H-pyran-6-carboxylic acid (which is Zanamivir, marketed as Relenza®) (FIG. 17A) and ethyl(3R,4R,5S)-5-amino-4-acetamido-3-(pentan-3-yloxy)-cyclohex-1-ene-1-carboxylate (which is oseltamivir, marketed as Tamiflu®) (FIG. 17C).
Figure 17B:
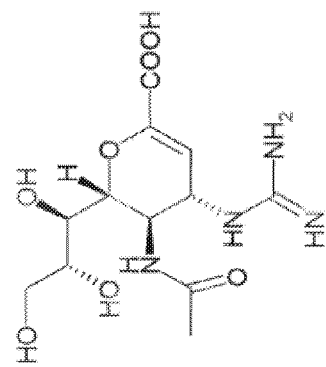
FIGS. 17B and 17D illustrate the immunohistochemistry analyses of the effects of Relenza® on BPLER cell migration (17D) and a control (17B). Both of these drugs are neuraminidase inhibitors.
Figure 17C:
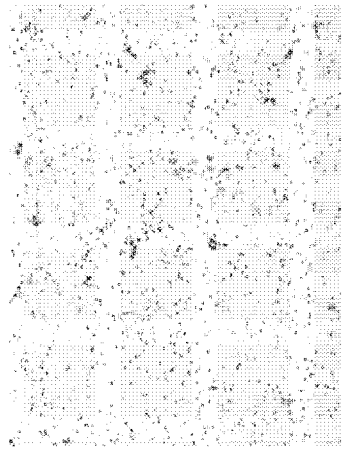
Figure 17D:
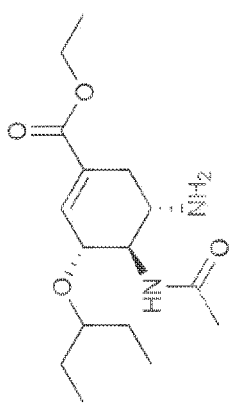

Using the NMR Data to Identify and Design Therapeutic Agents for Breast Cancer Therapy Enzymes such as CMAS are ideal candidates for small molecule drug inhibition. The enzyme mechanism of CMAS is FIG. 16A, where CMAS activates the hydroxy group of NANA in a divalent cation dependent manner, so that it can subsequently attack the alpha-phosphate of an incoming cytidine triphosphate (CTP) molecule to form a cytidine monophosphate-NANA (CMP-NANA) intermediate. Using the NANA scaffold, a substrate-based analog replacing the hydroxyl group with a fluorine was designed and synthesized (FIG. 16B). This substitution should theoretically maintain the ability of NANA to bind CMAS however, prevent the enzymatic reaction. In the presence of the CMAS inhibitor, using the previously described cell migration assay, it was shown that BPLER cells are no longer able to migrate (FIG. 16C). Using the NANA scaffold, we were able to rapidly design and synthesize a substrate based inhibitor that has effect in cell lines.

The F-NANA derivative synthesized had a slight chemical likeness to the FDA approved drugs Relenza and Tamiflu (FIG. 17). Relenza and Tamiflu are both designed to inhibit the influenza enzyme neuraminidase. Neuraminidase specifically cleaves NANA molecules on the cell-surface to facilitate viral entry into the cell. Neuraminidase and CMAS share NANA as a substrate, and hence these known influenza therapeutics were suspected to be inhibitors of CMAS. As shown in FIG. 17b, Relenza treatment of BPLER cells blocked cell migration. Both Relenza and Tamiflu are already FDA approved, marketed therapeutics, and pending positive results in mouse models, a rapid entry to clinical trial for cancer indications.

Figure 18A:
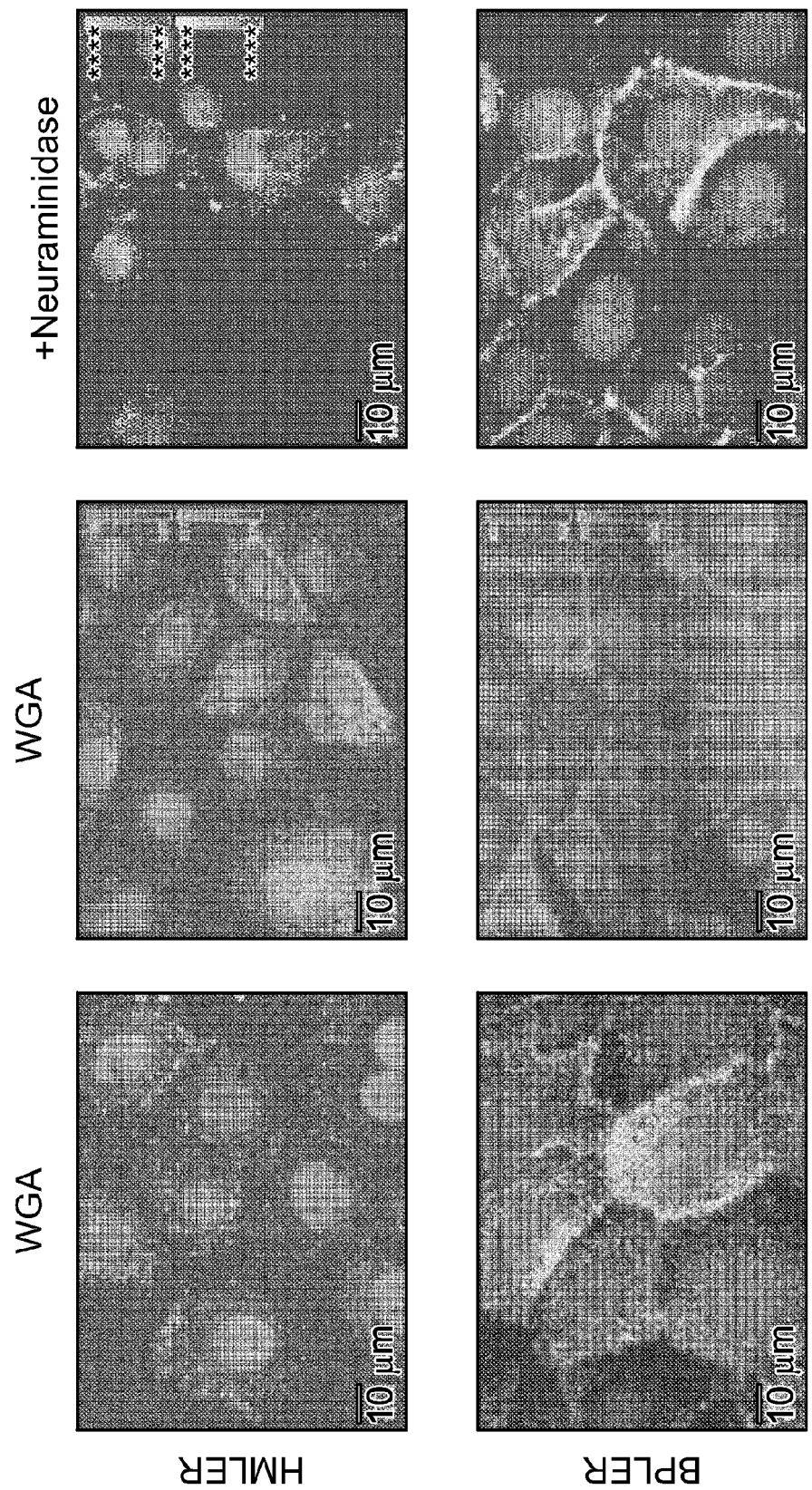
FIGS. 18A and 18B are immune-fluorescent microscopy images showing the expression of NANA in HMLER and BPLER cells in the absence and presence of neuraminidase (18A) and immunohistochemistry images of HMLER and BPLER cell migration in the presence and absence of neuraminidase (18B).
Figure 18B:
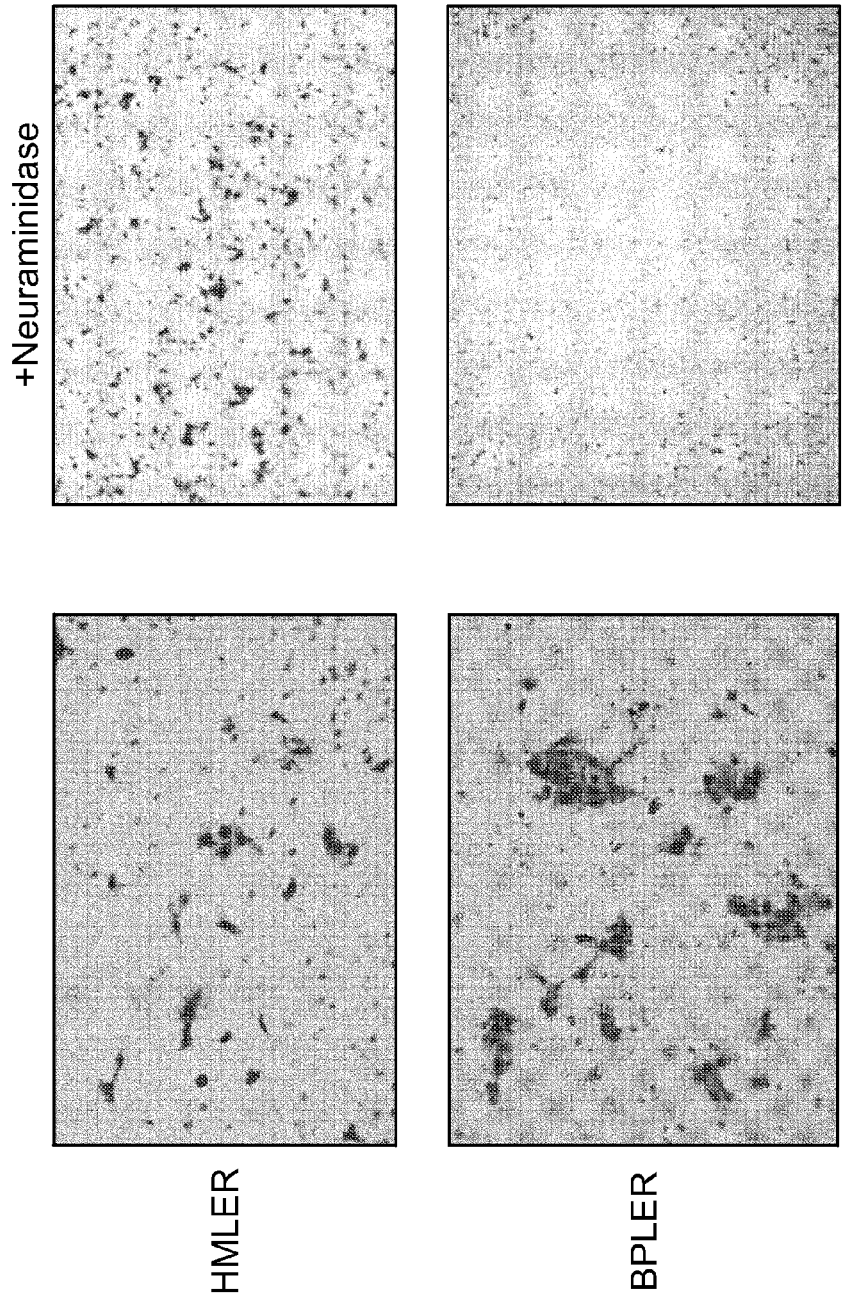

Neuraminidase itself is known to remove NANA from the cell surface. We suspected neuraminidase could be used to remove NANA from the surface of malignant cells and just like siRNAs against CMAS exert a similar effect on migration and tumor initiation. Pre-incubation of BPLER cells with active neuraminidase enzyme diminished NANA expression as determined by rhodamine labeled wheat germ agglutinin (WGA) microscopy (FIG. 18A). In addition, BPLER cells treated with neuraminidase were no longer able to migrate in the migration assay (FIG. 18B). Neuraminidase and flu-like molecules, including empty virions, may represent an innovative way to both detect tumor-initiating cells (influenza virions have a high affinity for NANA) and inhibit tumor initiation and metastasis by removing NANA from tumor populations.

Other Embodiments

It is to be understood that while the inventions have been described in conjunction with the detailed description thereof, the foregoing description is intended to illustrate and not limit the scope of the inventions, which are defined by the scope of the appended claims. Other aspects, advantages, and modifications are within the scope of the following claims.

What is claimed is:

1. A method for monitoring metabolism of a substrate within a given type of cell in a sample, the method comprising:
   a. culturing a given type of cell of a first sample with a substrate for a sufficient period of time to allow metabolic breakdown of the substrate into substrate metabolites, wherein at least a portion of the substrate is labeled with a nuclear magnetic resonance (NMR) stable isotope;
   b. harvesting the substrate metabolites from the cells of step (a) to obtain a second sample of substrate metabolites; and
   c. performing multi-dimensional NMR on the second sample of step (b) to determine a resonance spectrum of the metabolized substrate, wherein the resonance spectrum represents the metabolites of the substrate, and wherein the multi-dimensional NMR comprises any one of the following techniques:
      spectral width folding, random phase sampling in which a phase of a signal detector is randomly alternated between two values at different time points in an NMR signal, non-uniform sampling in which a parameter of an indirect domain of the multi-dimensional NMR is varied by an amount that changes with each experiment during performance of the multi-dimensional NMR, and data extension for enhanced dynamic range data reconstruction in which a number of data points in the indirect domain is increased after performing the multi-dimensional NMR.

2. The method of claim 1, wherein the multi-dimensional NMR comprises any two, in any combination, of the following techniques: spectral width folding, random phase sampling, non-uniform sampling, and data extension for enhanced dynamic range data reconstruction.

3. The method of claim 1, wherein the multi-dimensional NMR comprises all four of the following techniques: spectral width folding, random phase sampling, non-uniform sampling, and data extension for enhanced dynamic range data reconstruction.

4. The method of claim 1, wherein the substrate is labeled with a stable isotope and the multi-dimensional NMR comprises random phase sampling, non-uniform sampling, and data extension for enhanced dynamic range data reconstruction.

5. The method of claim 1, wherein the substrate metabolites that are present in the sample are not purified away from the other molecules in the sample.

6. The method of claim 1, wherein the substrate concentration within the population of cells is reduced for a period of time prior to loading the cells with the NMR-labeled substrate.

7. The method of claim 1, wherein the resonances of the metabolites of the labeled substrate are determined using NMR pulse programs or filtering techniques, or both, customized to the substrate.

8. The method of claim 1, wherein the number of cells within the population of cells is less than $2 \times 10^6$.

9. A method for identifying differentially expressed substrate metabolites between a first population of cells and a second population of cells, the method comprising:
   a. loading a first and a second population of cells with a nuclear magnetic resonance (NMR) stable isotope-labeled substrate;
   b. culturing the first and the second population of cells of step (a) for a sufficient period of time to allow metabolic breakdown of the substrate into substrate metabolites;
   c. harvesting the substrate metabolites from the first and the second population cells of step (b) to obtain a sample of substrate metabolites from each of the first and the second cell populations;
   d. performing multi-dimensional NMR on the sample of step (c) for each of the first and the second cell populations to determine a resonance spectrum of the metabolized substrate of the first population of cells and of the second population of cells, wherein the resonance spectrum represents the metabolites of the substrate, wherein the multi-dimensional NMR comprises any one of the following techniques: spectral width folding, random phase sampling in which a phase of a signal detector is randomly alternated between two values at different time points in an NMR signal, non-uniform sampling in which a parameter of an indirect domain of the multi-dimensional NMR is varied by an amount that changes with each experiment during performance of the multi-dimensional NMR, and data extension for enhanced dynamic range data reconstruction in which a number of data points in the indirect domain is increased after performing the multi-dimensional NMR; and
   e. comparing the resonance spectrum of the first population of cells with the resonance spectrum of the second population of cells to determine which resonances are differentially expressed, wherein the differentially expressed resonances provide a resonance signature that represents differentially expressed metabolites.

10. The method of claim 9, wherein the substrate is labeled with a stable isotope and the multi-dimensional NMR comprises any two, in any combination, of the following techniques: spectral width folding, random phase sampling, non-uniform sampling, and data extension for enhanced dynamic range data reconstruction.

11. The method of claim 9, wherein the substrate metabolites that are present in the sample are not purified away from the other molecules in the sample.

12. The method of claim 9, wherein the population of cells in each of the first cell population and second cell population is a heterogeneous population of cells, or is a homogeneous population of cells.

13. The method of claim 9, further comprising comparing the resonance signature of step (e) with a database of known resonance signatures to determine the molecular structure that the resonance signature represents, and thereby determine the substrate metabolites that are differentially expressed between the first and the second population of cells.

14. The method of claim 9, further comprising identifying a biosynthetic pathway involved in generation of the substrate metabolites and identifying proteins/enzymes of the pathway that may be targeted to modulate the differential expression of the metabolite, to thereby modulate the phenotype of the cells.

15. The method of claim 9, wherein the first population of cells and the second population of cells have different phenotypes.

16. The method of claim 9, wherein the first population of cells is a control population of cells and the second population of cells has been contacted with a test compound or agent.

* * * * *

SEQUENCE LISTING

```
<160> NUMBER OF SEQ ID NOS: 4

<210> SEQ ID NO 1
<211> LENGTH: 357
<212> TYPE: PRT
<213> ORGANISM: Homo sapiens

<400> SEQUENCE: 1

Met Pro Leu Glu Leu Glu Leu Cys Pro Gly Arg Trp Val Gly Gly Gln
 1               5                  10                  15

His Pro Cys Phe Ile Ile Ala Glu Ile Gly Gln Asn His Gln Gly Asp
                20                  25                  30

Leu Asp Val Ala Lys Arg Met Ile Arg Met Ala Lys Glu Cys Gly Ala
            35                  40                  45

Asp Cys Ala Lys Phe Gln Lys Ser Glu Leu Glu Phe Lys Phe Asn Arg
        50                  55                  60

Lys Ala Leu Glu Arg Pro Tyr Thr Ser Lys His Ser Trp Gly Lys Thr
    65                  70                  75                  80

Tyr Gly Glu His Lys Arg His Leu Glu Phe Ser His Asp Gln Tyr Arg
                85                  90                  95

Glu Leu Gln Arg Tyr Ala Glu Glu Val Gly Ile Phe Phe Thr Ala Ser
               100                 105                 110

Gly Met Asp Glu Met Ala Val Glu Phe Leu His Glu Leu Asn Val Pro
            115                 120                 125

Phe Phe Lys Val Gly Ser Gly Asp Thr Asn Asn Phe Pro Tyr Leu Glu
        130                 135                 140
```

```
Lys Thr Ala Lys Lys Gly Arg Pro Met Val Ile Ser Ser Gly Met Gln
145                 150                 155                 160

Ser Met Asp Thr Met Lys Gln Val Tyr Gln Ile Val Lys Pro Leu Asn
                165                 170                 175

Pro Asn Phe Cys Gln Cys Thr Ser Ala Tyr Pro Leu Gln Pro Glu Asp
            180                 185                 190

Val Asn Leu Arg Val Ile Ser Glu Tyr Gln Lys Leu Phe Pro Asp Ile
                195                 200                 205

Pro Ile Gly Tyr Ser Gly His Glu Thr Gly Ile Ala Ile Ser Val Ala
        210                 215                 220

Ala Val Ala Leu Gly Ala Lys Val Leu Glu Arg His Ile Thr Leu Asp
225                 230                 235                 240

Lys Thr Trp Lys Gly Ser Asp His Ser Ala Ser Leu Glu Pro Gly Glu
                245                 250                 255

Leu Ala Glu Leu Val Arg Ser Val Arg Leu Val Glu Arg Ala Leu Gly
            260                 265                 270

Ser Pro Thr Lys Gln Leu Leu Pro Cys Glu Met Ala Cys Asn Glu Lys
        275                 280                 285

Leu Gly Lys Ser Val Val Ala Lys Val Lys Ile Pro Glu Gly Thr Ile
290                 295                 300

Leu Thr Met Asp Met Leu Thr Val Lys Val Gly Glu Pro Lys Gly Tyr
305                 310                 315                 320

Pro Pro Glu Asp Ile Phe Asn Leu Val Gly Lys Val Leu Val Thr
                325                 330                 335

Val Glu Glu Asp Asp Thr Ile Met Glu Glu Leu Val Asp Asn His Gly
            340                 345                 350

Lys Lys Ile Lys Ser
        355

<210> SEQ ID NO 2
<211> LENGTH: 1253
<212> TYPE: DNA
<213> ORGANISM: Homo sapiens

<400> SEQUENCE: 2
cggcgaccgc gggctgacgt ggcggggctg gcgtgtgggt ctcgcagcgt tgctcacaga      60
acagagtaga ggcggcggcg gcggcggccg gacccagact ggtagtgagg ctttggaccc     120
cgagccgctg caatgccgct ggagctggag ctgtgtcccg gcgctgggt gggcgggcaa      180 cacccgtgct tcatcattgc cgagatcggc cagaaccacc agggcgacct ggacgtagcc     240
aagcgcatga tccgcatggc caaggagtgt ggggctgatt gtgctaagtt ccagaagagt     300
gagctagaat tcaagtttaa tcggaaagcc ttggagaggc catacacctc gaagcattcc     360
tgggggaaga cgtacgggga gcacaaacga catctggagt cagccatga ccagtacagg      420 gagctgcaga ggtacgccga ggaggttggg atcttcttca ctgcctctgg catggatgag     480
atggcagttg aattcctgca tgaactgaat gttccatttt tcaaagttgg atctggagac     540
actaataatt ttccttatct ggaaaagaca gccaaaaaag gtcgcccaat ggtgatctcc     600
agtgggatgc agtcaatgga caccatgaag caagtttatc agatcgtgaa gcccctcaac     660
cccaacttct gcttcttgca gtgtaccagc gcatacccgc tccagcctga ggacgtcaac     720
ctgcgggtca tctcggaata tcagaagctc tttcctgaca ttcccatagg gtattctggg     780
catgaaacag gcatagcgat atctgtggcc gcagtggctc tgggggccaa ggtgttggaa     840
```

```
cgtcacataa ctttggacaa gacctggaag gggagtgacc actcggcctc gctggagcct    900
ggagaactgg ccgagctggt gcggtcagtg cgtcttgtgg agcgtgccct gggctcccca    960
accaagcagc tgctgccctg tgagatggcc tgcaatgaga agctgggcaa gtctgtggtg   1020
gccaaagtga aaattccgga aggcaccatt ctaacaatgg acatgctcac cgtgaaggtg   1080
ggtgagccca aggctatcc tcctgaagac atctttaatc tagtgggcaa gaaggtcctg   1140
gtcactgttg aagaggatga caccatcatg aagaattgg tagataatca tggcaaaaaa   1200
aagtcttaaa aataaagtgc cattctctga attctcaaaa aaaaaaaaa aaa           1253
```

<210> SEQ ID NO 3
<211> LENGTH: 432
<212> TYPE: PRT
<213> ORGANISM: Homo sapiens

<400> SEQUENCE: 3

```
Met Asp Ser Val Glu Lys Gly Ala Ala Thr Ser Val Ser Asn Pro Arg
 1               5                  10                  15

Gly Arg Pro Ser Arg Gly Arg Pro Lys Leu Gln Arg Asn Ser Arg
            20                  25                  30

Gly Gly Gln Gly Arg Gly Val Glu Lys Pro Pro His Leu Ala Ala Leu
        35                  40                  45

Ile Leu Ala Arg Gly Gly Ser Lys Gly Ile Pro Leu Lys Asn Ile Lys
    50                  55                  60

His Leu Ala Gly Val Pro Leu Ile Gly Trp Val Leu Arg Ala Ala Leu
65                  70                  75                  80

Asp Ser Gly Ala Phe Gln Ser Val Trp Val Ser Thr Asp His Asp Glu
                85                  90                  95

Ile Glu Asn Val Ala Lys Gln Phe Gly Ala Gln Val His Arg Arg Ser
           100                 105                 110

Ser Glu Val Ser Lys Asp Ser Ser Thr Ser Leu Asp Ala Ile Ile Glu
       115                 120                 125

Phe Leu Asn Tyr His Asn Glu Val Asp Ile Val Gly Asn Ile Gln Ala
   130                 135                 140

Thr Ser Pro Cys Leu His Pro Thr Asp Leu Gln Lys Val Ala Glu Met
145                 150                 155                 160

Ile Arg Glu Glu Gly Tyr Asp Ser Val Phe Ser Val Val Arg Arg His
                165                 170                 175

Gln Phe Arg Trp Ser Glu Ile Gln Lys Gly Val Arg Glu Val Thr Glu
           180                 185                 190

Pro Leu Asn Leu Asn Pro Ala Lys Arg Pro Arg Arg Gln Asp Trp Asp
       195                 200                 205

Gly Glu Leu Tyr Glu Asn Gly Ser Phe Tyr Phe Ala Lys Arg His Leu
   210                 215                 220

Ile Glu Met Gly Tyr Leu Gln Gly Gly Lys Met Ala Tyr Tyr Glu Met
225                 230                 235                 240

Arg Ala Glu His Ser Val Asp Ile Asp Val Asp Ile Asp Trp Pro Ile
                245                 250                 255

Ala Glu Gln Arg Val Leu Arg Tyr Gly Tyr Phe Gly Lys Glu Lys Leu
           260                 265                 270

Lys Glu Ile Lys Leu Leu Val Cys Asn Ile Asp Gly Cys Leu Thr Asn
       275                 280                 285

Gly His Ile Tyr Val Ser Gly Asp Gln Lys Glu Ile Ile Ser Tyr Asp
   290                 295                 300
```

| | | | | | | | | | | | |
|---|---|---|---|---|---|---|---|---|---|---|---|
| Val | Lys | Asp | Ala | Ile | Gly | Ile | Ser | Leu | Leu | Lys | Ser | Gly | Ile | Glu |
| 305 | | | | 310 | | | | | 315 | | | | | 320 |

Val Arg Leu Ile Ser Glu Arg Ala Cys Ser Lys Gln Thr Leu Ser Ser
            325                 330                 335

Leu Lys Leu Asp Cys Lys Met Glu Val Ser Val Ser Asp Lys Leu Ala
            340                 345                 350

Val Val Asp Glu Trp Arg Lys Glu Met Gly Leu Cys Trp Lys Glu Val
            355                 360                 365

Ala Tyr Leu Gly Asn Glu Val Ser Asp Glu Glu Cys Leu Lys Arg Val
            370                 375                 380

Gly Leu Ser Gly Ala Pro Ala Asp Ala Cys Ser Thr Ala Gln Lys Ala
385                 390                 395                 400

Val Gly Tyr Ile Cys Lys Cys Asn Gly Gly Arg Gly Ala Ile Arg Glu
            405                 410                 415

Phe Ala Glu His Leu Leu Met Glu Lys Val Asn Asn Ser Cys Gln Lys
            420                 425                 430

<210> SEQ ID NO 4
<211> LENGTH: 1741
<212> TYPE: DNA
<213> ORGANISM: Homo sapiens

<400> SEQUENCE: 4

```
gatcgggcgg cgccgagctg aggtggtgag ggactagctc ccggatgtgg agaagctggg      60
gagaaggcgt gggaggaaga tggactcggt ggagaagggg gccgccacct ccgtctccaa     120
cccgcggggg cgaccgtccc ggggccggcc gccgaagctg cagcgcaact ctcgcggcgg     180
ccagggccga ggtgtggaga agcccccgca cctggcagcc ctaattctgg cccggggagg     240
cagcaaaggc atcccctga gaacattaa gcacctggcg ggggtcccgc tcattggctg      300
ggtcctgcgt gcggccctgg attcagggc cttccagagt gtatgggttt cgacagacca     360
tgatgaaatt gagaatgtgg ccaaacaatt tggtgcacaa gttcatcgaa gaagttctga     420
agtttcaaaa gacagctcta cctcactaga tgccatcata gaatttctta attatcataa     480
tgaggttgac attgtaggaa atattcaagc tacttctcca tgtttacatc ctactgatct     540
tcaaaaagtt gcagaaatga ttcgagaaga aggatatgat tctgttttct ctgttgtgag     600
acgccatcag tttcgatgga gtgaaattca gaaaggagtt cgtgaagtga ccgaacctct     660
gaatttaaat ccagctaaac ggcctcgtcg acaagactgg gatggagaat atatgaaaaa     720
tggctcattt tattttgcta aaagacattt gatagagatg ggttacttgc agggtggaaa     780
aatggcatac tacgaaatgc gagctgaaca tagtgtggat atagatgtgg atattgattg     840
gcctattgca gagcaaagag tattaagata tggctatttt ggcaaagaga agcttaagga     900
aataaaactt ttggtttgca atattgatgg atgtctcacc aatggccaca tttatgtatc     960
aggagaccaa aaagaaataa tatcttatga tgtaaaagat gctattggga taagtttatt    1020
aaagaaaagt ggtattgagg tgaggctaat ctcagaaagg gcctgttcaa agcagacgct    1080
gtcttcttta aaactggatt gcaaaatgga agtcagtgta tcagacaagc tagcagttgt    1140
agatgaatgg agaaaagaaa tgggcctgtg ctggaaagaa gtggcatatc ttggaaatga    1200
agtgtctgat gaagagtgct tgaagagagt gggcctaagt ggcgctcctg ctgatgcctg    1260
ttctactgcc cagaaggctg ttggatacat ttgcaaatgt aatggtggcc gtggtgccat    1320
ccgagaattt gcagagcaca tttgcctact aatggaaaag gttaataatt catgccaaaa    1380
atagaaatta gcgtaatatt gagaaaaaaa tgatacagcc ttcttcagcc agtttgcttt    1440
```

-continued

```
tatttttgat taagtaaatt ccatgttgta atgttacaga gagtgtgatt tggtttgtga    1500
tatatatata ttgtgctcta cttttctctt tacgcaagat aattatttag agactgatta    1560
cagtctttct cagatttta gtaaatgcaa gtaagaacat catcaaagtt cactttgtat     1620
tgtaccctgt aaaactgtgt gtttgtgtgc tttcaaagat gttgggattt tatttatctg    1680
gggacagtgt gtatggtaag acatgcsctt ctattaataa aactacattt ctcaaacttg    1740
a                                                                    1741
```